US010806889B2

(12) United States Patent
Sweeney et al.

(10) Patent No.: US 10,806,889 B2
(45) Date of Patent: Oct. 20, 2020

(54) TREATMENT OF RESPIRATORY CONDITIONS

(71) Applicant: ResMed Pty Ltd, Bella Vista (AU)

(72) Inventors: Peter John Sweeney, Greenwich (AU); Adam Vivian Benjafield, Thornleigh (AU); Steven Paul Farrugia, Lugarno (AU); Dieter Heidmann, Cherrybrook (AU); Glenn Richards, Clevedon (NZ); Paul Jan Klasek, Bonnyrigg Heights (AU)

(73) Assignee: ResMed Pty Ltd, Bella Vista, NSW (AU)

( * ) Notice: Subject to any disclaimer, the term of this patent is extended or adjusted under 35 U.S.C. 154(b) by 0 days.

(21) Appl. No.: 16/259,743

(22) Filed: Jan. 28, 2019

(65) Prior Publication Data
US 2019/0314597 A1  Oct. 17, 2019

Related U.S. Application Data

(63) Continuation of application No. 16/258,176, filed on Jan. 25, 2019, which is a continuation of application
(Continued)

(51) Int. Cl.
*A61M 16/16* (2006.01)
*A61M 16/00* (2006.01)
(Continued)

(52) U.S. Cl.
CPC ........ *A61M 16/16* (2013.01); *A61M 16/0069* (2014.02); *A61M 16/024* (2017.08);
(Continued)

(58) Field of Classification Search
CPC ..... A61M 16/00–0012; A61M 16/0051–0075; A61M 16/16–168;
(Continued)

(56) References Cited

U.S. PATENT DOCUMENTS 322,318 A  7/1885  Faucet
485,127 A  10/1892  Lynch
(Continued)

FOREIGN PATENT DOCUMENTS

AT  397727  6/1994
AU  200065475  4/2001
(Continued)

OTHER PUBLICATIONS

ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.
(Continued)

*Primary Examiner* — Timothy A Stanis
*Assistant Examiner* — Ned T Heffner
(74) *Attorney, Agent, or Firm* — Fish & Richardson P.C.

(57) ABSTRACT

A device (102) provides respiratory treatment for SDB (including mild OSA) and other respiratory conditions. A flow generator warms and humidifies gas at controlled flow levels. For example, the device (102) delivers breathable gas to the upper airway at flow rates of about 10-35 Liters/minute. Levels of flow rate, temperature and/or humidification of the device may be automatically adjusted in response to the detection of SDB events. The device may also automatically deliver adjustments of any of the levels in accordance with detected phases of respiratory cycles. In some embodiments, the device automatically delivers distinct levels to either of the nares based on independent control of flow to each nare. A warm-up procedure controls temperature and humidity at a desired target during a ramp-up of flow to the set therapy level. A cool-down procedure controls temperature above the dewpoint to avoid condensation internal to the device and patient interface.

29 Claims, 24 Drawing Sheets

Related U.S. Application Data

No. 12/995,561, filed as application No. PCT/AU2009/000671 on May 28, 2009, now Pat. No. 10,350,379.

(60) Provisional application No. 61/117,375, filed on Nov. 24, 2008, provisional application No. 61/059,084, filed on Jun. 5, 2008.

(51) Int. Cl.
    *A61M 16/06* (2006.01)
    *A61M 16/10* (2006.01)
    *A61M 16/20* (2006.01)
    *A61M 16/08* (2006.01)

(52) U.S. Cl.
    CPC .... *A61M 16/0688* (2014.02); *A61M 16/1095* (2014.02); *A61M 16/161* (2014.02); *A61M 16/204* (2014.02); *A61M 16/0066* (2013.01); *A61M 16/0666* (2013.01); *A61M 16/0825* (2014.02); *A61M 16/107* (2014.02); *A61M 2016/0021* (2013.01); *A61M 2016/0027* (2013.01); *A61M 2016/0039* (2013.01); *A61M 2202/0208* (2013.01); *A61M 2205/18* (2013.01); *A61M 2205/3368* (2013.01); *A61M 2205/502* (2013.01); *A61M 2205/8206* (2013.01); *A61M 2205/8237* (2013.01)

(58) Field of Classification Search
    CPC ... A61M 16/20–207; A61M 2016/0015–0042; A61M 16/12
    See application file for complete search history.

(56) References Cited

U.S. PATENT DOCUMENTS

| | | |
|---|---|---|
| 933,301 A | 9/1909 | Hartman |
| 985,279 A | 2/1911 | Ohlson et al. |
| 1,085,833 A | 2/1914 | Wilson |
| 1,710,160 A | 2/1925 | Gibbs |
| 1,813,959 A | 7/1931 | Romanoff |
| 1,974,843 A | 9/1934 | Blashfield |
| RE19,826 E | 1/1936 | Aisenstein |
| 2,126,755 A | 8/1938 | Dreyfus |
| 2,130,555 A | 9/1938 | Malcom |
| 2,220,669 A | 11/1940 | Allen et al. |
| 2,228,218 A | 1/1941 | Schwartz |
| 2,578,621 A | 12/1951 | Yant |
| 2,706,983 A | 4/1955 | Matheson et al. |
| 2,780,708 A | 2/1957 | Glynn et al. |
| 2,945,619 A | 7/1960 | McLure et al. |
| 3,171,353 A | 3/1965 | McMahan |
| 3,316,910 A | 5/1967 | Davis et al. |
| 3,330,273 A | 7/1967 | Bennett |
| 3,424,633 A | 1/1969 | Corrigall et al. |
| 3,584,401 A | 6/1971 | Cryer et al. |
| 3,612,710 A | 10/1971 | Mount |
| 3,620,638 A | 11/1971 | Kaye et al. |
| 3,638,926 A | 2/1972 | Melville et al. |
| 3,659,604 A | 5/1972 | Melville et al. |
| 3,690,317 A | 9/1972 | Millman |
| 3,746,467 A | 7/1973 | Buse |
| 3,768,468 A | 10/1973 | Cox |
| 3,786,809 A | 1/1974 | Kitrilakis |
| 3,806,102 A | 4/1974 | Valenta et al. |
| 3,864,440 A | 2/1975 | Giocoechea |
| 3,912,795 A | 10/1975 | Jackson |
| 3,954,920 A | 5/1976 | Heath |
| 4,037,994 A | 7/1977 | Bird |
| 4,051,205 A | 9/1977 | Grant |
| 4,060,337 A | 11/1977 | Bell, III |
| 4,152,379 A | 5/1979 | Suhr |
| 4,171,190 A | 10/1979 | Hudson |
| 4,222,971 A | 9/1980 | Eiert |
| 4,229,142 A | 10/1980 | Le Dall et al. |
| 4,237,080 A | 12/1980 | Eliott |
| 4,243,396 A | 1/1981 | Cronenberg |
| 4,249,527 A | 2/1981 | Ko et al. |
| 4,278,082 A | 7/1981 | Blackmer |
| 4,281,651 A | 8/1981 | Cox |
| 4,336,798 A | 6/1982 | Beran |
| 4,369,777 A | 1/1983 | Lwoff et al. |
| 4,383,800 A | 5/1983 | Becker et al. |
| 4,511,355 A | 4/1985 | Franetzki et al. |
| 4,523,896 A | 6/1985 | Lhenry et al. |
| 4,532,088 A | 7/1985 | Miller |
| 4,576,616 A | 3/1986 | Mottram et al. |
| 4,588,425 A | 5/1986 | Usry et al. |
| 4,621,632 A | 11/1986 | Bartels et al. |
| 4,637,384 A | 1/1987 | Schroeder |
| 4,643,183 A | 2/1987 | Seilinger |
| 4,657,713 A | 4/1987 | Miller |
| 4,676,241 A | 6/1987 | Webb et al. |
| 4,686,354 A | 8/1987 | Makin |
| 4,753,758 A | 6/1988 | Miller |
| 4,782,832 A | 11/1988 | Trimble et al. |
| 4,799,287 A | 1/1989 | Belanger et al. |
| 4,802,819 A | 2/1989 | Bevington et al. |
| 4,807,616 A | 2/1989 | Adahan |
| 4,838,258 A | 6/1989 | Dryden et al. |
| 4,906,417 A | 3/1990 | Gentry |
| 4,913,140 A | 4/1990 | Orec et al. |
| 4,919,128 A | 4/1990 | Kopala et al. |
| 4,921,642 A | 5/1990 | LaTorraca |
| 4,926,856 A | 5/1990 | Cambio, Jr. et al. |
| 4,941,469 A | 7/1990 | Adahan |
| 4,944,310 A | 7/1990 | Sullivan |
| 4,946,348 A | 8/1990 | Yapp |
| 4,953,546 A | 9/1990 | Blackmer et al. |
| 4,967,744 A | 11/1990 | Chua |
| 4,973,234 A | 11/1990 | Swenson |
| 4,989,599 A | 2/1991 | Carter |
| 4,993,411 A | 2/1991 | Callaway |
| 5,031,612 A | 7/1991 | Clementi |
| 5,042,478 A | 8/1991 | Kopala et al. |
| 5,062,421 A | 11/1991 | Burns et al. |
| 5,065,756 A | 11/1991 | Rapoport |
| 5,097,424 A | 3/1992 | Ginevri et al. |
| 5,101,820 A | 4/1992 | Christopher |
| 5,127,800 A | 7/1992 | Hyll et al. |
| 5,199,009 A | 3/1993 | Svast |
| 5,231,979 A | 8/1993 | Rose et al. |
| 5,237,987 A | 8/1993 | Anderson et al. |
| 5,243,971 A | 9/1993 | Sullivan et al. |
| 5,245,995 A | 9/1993 | Sullivan et al. |
| 5,271,391 A | 12/1993 | Graves |
| 5,329,939 A | 7/1994 | Howe |
| 5,349,946 A | 9/1994 | McComb |
| 5,391,063 A | 2/1995 | Hantle et al. |
| 5,392,770 A | 2/1995 | Clawson et al. |
| 5,443,061 A | 8/1995 | Champain et al. |
| 5,445,143 A | 8/1995 | Sims |
| 5,474,112 A | 12/1995 | Carola |
| 5,482,031 A | 1/1996 | Lambert |
| 5,490,502 A | 2/1996 | Rapoport et al. |
| 5,533,506 A | 7/1996 | Wood |
| 5,536,140 A | 7/1996 | Wagner et al. |
| 5,537,997 A | 7/1996 | Mechlenburg et al. |
| 5,558,084 A | 9/1996 | Daniell et al. |
| 5,564,415 A | 10/1996 | Dobson et al. |
| 5,577,496 A | 11/1996 | Blackwood et al. |
| 5,588,423 A | 12/1996 | Smith |
| 5,598,837 A | 2/1997 | Sirianne, Jr. et al. |
| 5,605,444 A | 2/1997 | Paton et al. |
| 5,651,775 A | 7/1997 | Walker et al. |
| 5,655,522 A | 8/1997 | Mechlenburg et al. |
| 5,657,752 A | 8/1997 | Landis et al. |
| 5,662,101 A | 9/1997 | Ogden et al. |
| 5,673,687 A | 10/1997 | Dobson et al. |
| 5,682,881 A | 11/1997 | Winthrop et al. |
| 5,692,497 A | 12/1997 | Schnitzer et al. |
| 5,701,883 A | 12/1997 | Hete et al. |

(56) References Cited

U.S. PATENT DOCUMENTS

| | | |
|---|---|---|
| 5,704,345 A | 1/1998 | Berthon-Jones |
| 5,724,965 A | 3/1998 | Handke et al. |
| 5,746,201 A | 5/1998 | Kidd |
| 5,794,219 A | 8/1998 | Brown |
| 5,822,715 A | 10/1998 | Worthington et al. |
| 5,828,943 A | 10/1998 | Brown |
| 5,832,448 A | 11/1998 | Brown |
| 5,848,592 A | 12/1998 | Sibley |
| 5,870,283 A | 2/1999 | Maeda et al. |
| 5,879,163 A | 3/1999 | Brown et al. |
| 5,887,133 A | 3/1999 | Brown et al. |
| 5,888,053 A | 3/1999 | Kobayashi et al. |
| 5,897,493 A | 4/1999 | Brown |
| 5,899,855 A | 5/1999 | Brown |
| 5,913,310 A | 6/1999 | Brown |
| 5,916,493 A | 6/1999 | Miller |
| 5,918,603 A | 7/1999 | Brown |
| 5,921,239 A | 7/1999 | McCall et al. |
| 5,933,136 A | 8/1999 | Brown |
| 5,940,801 A | 8/1999 | Brown |
| 5,943,473 A | 8/1999 | Levine |
| 5,951,300 A | 9/1999 | Brown |
| 5,956,501 A | 9/1999 | Brown |
| 5,960,403 A | 9/1999 | Brown |
| 5,985,559 A | 11/1999 | Brown |
| 5,997,476 A | 12/1999 | Brown |
| D419,658 S | 1/2000 | Matchett et al. |
| 6,012,455 A | 1/2000 | Goldstein |
| 6,016,804 A | 1/2000 | Gleason et al. |
| 6,023,686 A | 2/2000 | Brown |
| 6,024,088 A | 2/2000 | Ishikawa et al. |
| 6,032,119 A | 2/2000 | Brown et al. |
| 6,050,260 A | 4/2000 | Daniell et al. |
| 6,101,478 A | 8/2000 | Brown |
| 6,109,865 A | 8/2000 | Ishikawa |
| 6,111,748 A | 8/2000 | Bhatia |
| 6,119,693 A | 9/2000 | Kwok et al. |
| 6,119,694 A | 9/2000 | Correa et al. |
| 6,129,524 A | 10/2000 | Woollenweber et al. |
| 6,131,571 A | 10/2000 | Lampotang et al. |
| 6,135,432 A | 10/2000 | Hebblewhite et al. |
| 6,144,837 A | 11/2000 | Quy |
| 6,152,132 A | 11/2000 | Psaros |
| 6,158,978 A | 12/2000 | Norbury, Jr. |
| 6,161,095 A | 12/2000 | Brown |
| 6,185,095 B1 | 2/2001 | Helot et al. |
| 6,189,870 B1 | 2/2001 | Withall |
| 6,192,886 B1 | 2/2001 | Rudolph |
| 6,202,991 B1 | 3/2001 | Coniglio et al. |
| 6,210,116 B1 | 4/2001 | Kuczaj et al. |
| 6,213,119 B1 | 4/2001 | Brydon et al. |
| 6,216,691 B1 | 4/2001 | Kenyon et al. |
| 6,231,053 B1 | 5/2001 | Wakamatsu |
| 6,240,921 B1 | 6/2001 | Brydon et al. |
| 6,257,171 B1 | 7/2001 | Rivard |
| 6,279,574 B1 | 8/2001 | Richardson et al. |
| 6,308,706 B1 | 10/2001 | Lammers et al. |
| 6,325,063 B1 | 12/2001 | Volgyesi |
| 6,332,462 B1 | 12/2001 | Krohn |
| 6,338,473 B1 | 1/2002 | Hebblewhite et al. |
| 6,340,288 B1 | 1/2002 | Hulkkonen et al. |
| 6,345,538 B1 | 2/2002 | Krahbichler et al. |
| 6,349,724 B1 * | 2/2002 | Burton ............ A61M 16/0057 128/204.18 |
| D454,393 S | 3/2002 | Lynch et al. |
| 6,363,933 B1 | 4/2002 | Berthon-Jones |
| 6,367,472 B1 | 4/2002 | Koch |
| 6,374,826 B1 | 4/2002 | Gunaratnam et al. |
| 6,397,841 B1 | 5/2002 | Kenyon et al. |
| 6,398,197 B1 | 6/2002 | Dickinson et al. |
| 6,398,739 B1 | 6/2002 | Sullivan et al. |
| 6,412,488 B1 | 7/2002 | Barnett et al. |
| 6,431,172 B1 | 8/2002 | Bordewick |
| 6,435,180 B1 | 8/2002 | Hewson et al. |
| 6,435,181 B1 | 8/2002 | Jones, Jr. et al. |
| 6,457,473 B1 | 10/2002 | Brostrom et al. |
| 6,467,477 B1 | 10/2002 | Frank et al. |
| 6,467,483 B1 | 10/2002 | Kopacko et al. |
| 6,471,493 B2 | 10/2002 | Choi et al. |
| 6,478,026 B1 | 11/2002 | Wood |
| D467,335 S | 12/2002 | Lithgow et al. |
| D468,011 S | 12/2002 | Lithgow et al. |
| D468,017 S | 12/2002 | McCombs |
| 6,499,954 B1 | 12/2002 | Adonakis |
| 6,514,053 B2 | 2/2003 | Takura et al. |
| 6,516,801 B2 | 2/2003 | Boussignac |
| 6,523,538 B1 | 2/2003 | Wilkefeldt |
| 6,530,373 B1 | 3/2003 | Patron et al. |
| 6,532,961 B1 | 3/2003 | Kwok et al. |
| 6,543,449 B1 | 4/2003 | Woodring et al. |
| 6,554,260 B1 | 4/2003 | Lipscombe et al. |
| 6,561,190 B1 | 5/2003 | Kwok |
| 6,581,594 B1 | 6/2003 | Drew et al. |
| 6,591,834 B1 | 7/2003 | Colla et al. |
| 6,604,390 B1 | 8/2003 | Nooner |
| 6,615,444 B2 | 9/2003 | McGill et al. |
| 6,622,724 B1 | 9/2003 | Truitt et al. |
| 6,629,527 B1 | 10/2003 | Estes et al. |
| 6,631,718 B1 | 10/2003 | Lovell |
| 6,635,021 B1 | 10/2003 | Sullivan et al. |
| 6,672,300 B1 | 1/2004 | Grant |
| 6,691,707 B1 | 2/2004 | Gunaratnam et al. |
| D487,311 S | 3/2004 | Lithgow et al. |
| 6,718,974 B1 | 4/2004 | Moberg |
| D493,520 S | 7/2004 | Bertinetti et al. |
| D493,884 S | 8/2004 | Virr et al. |
| 6,770,037 B2 | 8/2004 | Sullivan et al. |
| 6,772,999 B2 | 8/2004 | Lipscombe et al. |
| 6,775,882 B2 | 8/2004 | Murphy et al. |
| 6,776,163 B2 | 8/2004 | Dougill et al. |
| 6,796,308 B2 | 9/2004 | Gunaratnam et al. |
| D498,527 S | 11/2004 | Virr et al. |
| 6,821,095 B2 | 11/2004 | Dooley et al. |
| 6,823,869 B2 | 11/2004 | Raje et al. |
| 6,827,340 B2 | 12/2004 | Austin et al. |
| 6,837,260 B1 | 1/2005 | Kuehn |
| 6,851,425 B2 | 2/2005 | Jaffre et al. |
| 6,874,771 B2 | 4/2005 | Birdsell et al. |
| 6,881,033 B2 | 4/2005 | Makinson et al. |
| 6,896,478 B2 | 5/2005 | Botros et al. |
| 6,907,882 B2 | 6/2005 | Ging et al. |
| 6,910,483 B2 | 6/2005 | Daly et al. |
| 6,918,389 B2 | 7/2005 | Seakins et al. |
| 6,935,337 B2 | 8/2005 | Virr et al. |
| 6,994,089 B2 | 2/2006 | Wood |
| 7,004,908 B2 | 2/2006 | Sullivan et al. |
| 7,007,696 B2 | 3/2006 | Palkon et al. |
| 7,080,645 B2 | 7/2006 | Genger et al. |
| 7,096,864 B1 | 8/2006 | Mayer et al. |
| 7,108,482 B2 | 9/2006 | Chapman |
| 7,111,624 B2 | 9/2006 | Thudor et al. |
| 7,137,388 B2 | 11/2006 | Virr et al. |
| 7,141,021 B2 | 11/2006 | Sullivan et al. |
| 7,178,525 B2 | 2/2007 | Matula, Jr. et al. |
| 7,178,528 B2 | 2/2007 | Lau et al. |
| 7,210,481 B1 | 5/2007 | Lovell et al. |
| 7,210,903 B2 | 5/2007 | Lyons |
| 7,219,669 B1 | 5/2007 | Lovell et al. |
| 7,225,809 B1 | 6/2007 | Bowen et al. |
| 7,314,046 B2 | 1/2008 | Schroeder et al. |
| 7,353,827 B2 | 4/2008 | Geist |
| 7,357,136 B2 | 4/2008 | Ho et al. |
| 7,413,173 B2 | 8/2008 | DiMatteo et al. |
| 7,614,398 B2 | 11/2009 | Virr et al. |
| 7,616,871 B2 | 11/2009 | Kramer |
| 7,658,189 B2 | 2/2010 | Davidson et al. |
| 7,677,246 B2 | 3/2010 | Kepler et al. |
| 7,748,381 B2 | 7/2010 | Croll et al. |
| 7,827,990 B1 | 11/2010 | Melidis et al. |
| 7,938,113 B2 | 5/2011 | Weinstein et al. |
| 8,091,547 B2 | 1/2012 | Thudor et al. |
| 8,171,935 B2 | 5/2012 | Cortez, Jr. et al. |
| 8,177,914 B2 | 5/2012 | Peters |
| 8,220,458 B2 | 7/2012 | Landis et al. |

(56) References Cited

U.S. PATENT DOCUMENTS

| | | |
|---|---|---|
| 8,220,463 B2 | 7/2012 | White et al. |
| 8,225,796 B2 | 7/2012 | Davenport et al. |
| 8,333,195 B2 | 12/2012 | Cortez, Jr. et al. |
| 8,443,807 B2 | 5/2013 | McAuley et al. |
| 8,479,741 B2 | 7/2013 | McAuley et al. |
| 8,490,621 B2 | 7/2013 | Radomski et al. |
| RE44,453 E | 8/2013 | Virr et al. |
| 8,517,012 B2 | 8/2013 | Daly et al. |
| 8,550,072 B2 | 10/2013 | Thudor et al. |
| 8,714,157 B2 | 5/2014 | McAuley et al. |
| 8,733,353 B2 | 5/2014 | Kramer et al. |
| 8,905,023 B2 | 12/2014 | Niland et al. |
| 8,944,061 B2 | 2/2015 | D'Souza et al. |
| 8,950,404 B2 | 2/2015 | Formica et al. |
| 8,960,196 B2 | 2/2015 | Henry |
| 9,027,556 B2 | 5/2015 | Ng et al. |
| 9,119,931 B2 | 9/2015 | D'Souza et al. |
| 9,242,062 B2 | 1/2016 | Melidis et al. |
| 9,333,315 B2 | 5/2016 | McAuley et al. |
| 9,381,316 B2 | 7/2016 | Ng et al. |
| 9,517,317 B2 | 12/2016 | McAuley et al. |
| 9,539,405 B2 | 1/2017 | McAuley et al. |
| 9,907,922 B2 | 3/2018 | Stephenson et al. |
| 9,907,923 B2 | 3/2018 | Stephenson et al. |
| 9,974,914 B2 | 5/2018 | McAuley et al. |
| 2001/0017134 A1 | 8/2001 | Bahr |
| 2002/0020416 A1 | 2/2002 | Namey |
| 2002/0020930 A1 | 2/2002 | Austin et al. |
| 2002/0022973 A1 | 2/2002 | Sun et al. |
| 2002/0029780 A1 | 3/2002 | Frater et al. |
| 2002/0056453 A1 | 5/2002 | Klopp et al. |
| 2002/0096173 A1 | 7/2002 | Berthon-Jones et al. |
| 2002/0112725 A1* | 8/2002 | Thudor .............. A61M 16/16 128/204.18 |
| 2002/0119044 A1 | 8/2002 | O'Connor, Jr. et al. |
| 2002/0159897 A1 | 10/2002 | Kegg et al. |
| 2003/0000533 A1* | 1/2003 | Olsen ............... A61M 16/06 128/206.21 |
| 2003/0029454 A1 | 2/2003 | Gelinas et al. |
| 2003/0062045 A1 | 4/2003 | Woodring et al. |
| 2003/0082016 A1 | 5/2003 | Eavenson, Sr. et al. |
| 2003/0084900 A1 | 5/2003 | Leclerc et al. |
| 2003/0115085 A1 | 6/2003 | Satoh |
| 2003/0181917 A1 | 9/2003 | Gertner |
| 2003/0196655 A1 | 10/2003 | Ging et al. |
| 2003/0196658 A1 | 10/2003 | Ging et al. |
| 2003/0208465 A1 | 11/2003 | Yurko et al. |
| 2003/0209246 A1 | 11/2003 | Schroeder et al. |
| 2003/0230308 A1 | 12/2003 | Linden |
| 2004/0016430 A1 | 1/2004 | Makinson et al. |
| 2004/0025882 A1 | 2/2004 | Madaus et al. |
| 2004/0035422 A1 | 2/2004 | Truitt et al. |
| 2004/0041342 A1 | 3/2004 | Frieman |
| 2004/0055597 A1 | 3/2004 | Virr et al. |
| 2004/0060559 A1 | 4/2004 | Virr et al. |
| 2004/0067333 A1 | 4/2004 | Amarasinghe |
| 2004/0118406 A1 | 6/2004 | Lithgow et al. |
| 2004/0173210 A1 | 9/2004 | Campbell |
| 2004/0182386 A1 | 9/2004 | Meier |
| 2004/0182398 A1 | 9/2004 | Sprinkle et al. |
| 2004/0211428 A1 | 10/2004 | Jones, Jr. et al. |
| 2004/0226566 A1 | 11/2004 | Gunaratnam et al. |
| 2004/0255949 A1 | 12/2004 | Lang et al. |
| 2004/0261797 A1 | 12/2004 | White et al. |
| 2005/0001152 A1 | 1/2005 | Stewart et al. |
| 2005/0005937 A1 | 1/2005 | Farrugia et al. |
| 2005/0011523 A1 | 1/2005 | Aylsworth et al. |
| 2005/0011524 A1 | 1/2005 | Thomlinson et al. |
| 2005/0028822 A1 | 2/2005 | Sleeper et al. |
| 2005/0103339 A1 | 5/2005 | Daly et al. |
| 2005/0121033 A1 | 6/2005 | Starr et al. |
| 2005/0143617 A1 | 6/2005 | Auphan |
| 2005/0155604 A1 | 7/2005 | Ging et al. |
| 2005/0178383 A1 | 8/2005 | Mackie et al. |
| 2005/0217673 A1 | 10/2005 | Daly et al. |
| 2005/0284484 A1 | 12/2005 | Curti et al. |
| 2006/0000475 A1 | 1/2006 | Matthews et al. |
| 2006/0042629 A1 | 3/2006 | Geist |
| 2006/0060200 A1* | 3/2006 | Ho ..................... A61M 16/0683 128/206.24 |
| 2006/0078423 A1 | 4/2006 | Zheng |
| 2006/0113690 A1* | 6/2006 | Huddart ............ A61M 16/1075 261/129 |
| 2006/0118117 A1 | 6/2006 | Berthon-Jones et al. |
| 2006/0124131 A1 | 6/2006 | Chandran et al. |
| 2006/0169281 A1 | 8/2006 | Aylsworth et al. |
| 2006/0191531 A1 | 8/2006 | Mayer et al. |
| 2006/0201504 A1 | 9/2006 | Singhal et al. |
| 2006/0201514 A1 | 9/2006 | Jones et al. |
| 2006/0237005 A1 | 10/2006 | Virr et al. |
| 2006/0272646 A1 | 12/2006 | Ho et al. |
| 2007/0036662 A1 | 2/2007 | Pesola et al. |
| 2007/0044804 A1 | 3/2007 | Matula, Jr. et al. |
| 2007/0107737 A1* | 5/2007 | Landis ............... A61M 16/0666 128/207.18 |
| 2007/0134085 A1 | 6/2007 | Daly et al. |
| 2007/0175473 A1 | 8/2007 | Lewis et al. |
| 2007/0175480 A1 | 8/2007 | Gradon et al. |
| 2007/0272240 A1 | 11/2007 | Aylsworth et al. |
| 2008/0006277 A1 | 1/2008 | Worboys et al. |
| 2008/0027344 A1 | 1/2008 | Terry |
| 2008/0035202 A1 | 2/2008 | Lee et al. |
| 2008/0041393 A1 | 2/2008 | Bracken |
| 2008/0051674 A1 | 2/2008 | Davenport et al. |
| 2008/0110464 A1 | 5/2008 | Davidson et al. |
| 2009/0044808 A1 | 2/2009 | Guney et al. |
| 2009/0229606 A1 | 9/2009 | Tang et al. |
| 2009/0253995 A1 | 10/2009 | Lewis et al. |
| 2009/0320851 A1 | 12/2009 | Selvarajan et al. |
| 2010/0132707 A1 | 6/2010 | Muller |
| 2010/0229867 A1 | 9/2010 | Bertinetti et al. |
| 2011/0072553 A1 | 3/2011 | Ho |
| 2011/0108033 A1 | 5/2011 | Schaetzl |
| 2011/0110774 A1 | 5/2011 | Horng et al. |
| 2011/0125052 A1 | 5/2011 | Davenport et al. |
| 2011/0253136 A1 | 10/2011 | Sweeney et al. |
| 2014/0083430 A1 | 3/2014 | Matula, Jr. et al. |
| 2019/0209802 A1 | 7/2019 | Virr et al. |

FOREIGN PATENT DOCUMENTS

| | | |
|---|---|---|
| CN | 1886167 | 9/2012 |
| DE | 275612 | 1/1913 |
| DE | 2406679 | 8/1975 |
| DE | 3011287 | 1/1981 |
| DE | 3005094 | 8/1981 |
| DE | 3623162 | 1/1987 |
| DE | 3823242 | 2/1990 |
| DE | 9014848 | 2/1991 |
| DE | 4138098 | 5/1993 |
| DE | 4244493 | 7/1993 |
| DE | 3789221 | 8/1994 |
| DE | 9317450 | 9/1994 |
| DE | 9409231 | 11/1994 |
| DE | 19630466 | 5/1998 |
| DE | 69409024 | 10/1998 |
| DE | 19715581 | 2/1999 |
| DE | 29817685 | 5/1999 |
| DE | 29909611 | 9/1999 |
| DE | 19936499 | 2/2001 |
| DE | 10016005 | 12/2001 |
| DE | 102005007773 | 9/2005 |
| DE | 19515739 | 11/2007 |
| DE | 102007028742 | 12/2008 |
| EP | 0201985 | 11/1986 |
| EP | 0274996 | 7/1988 |
| EP | 0376584 | 7/1990 |
| EP | 0589429 | 3/1994 |
| EP | 0845277 | 6/1998 |
| EP | 0893750 | 1/1999 |
| EP | 0903160 | 3/1999 |
| EP | 1023912 | 8/2000 |
| EP | 1055431 | 11/2000 |
| EP | 1087322 | 3/2001 |

(56) References Cited

FOREIGN PATENT DOCUMENTS

| | | |
|---|---|---|
| EP | 1318307 | 6/2003 |
| EP | 1374938 | 1/2004 |
| EP | 0885623 | 3/2004 |
| EP | 1270037 | 9/2004 |
| EP | 1899016 | 6/2006 |
| EP | 2112938 | 2/2007 |
| EP | 1968673 | 9/2009 |
| EP | 2317150 | 10/2009 |
| EP | 2113274 | 4/2016 |
| EP | 3434332 | 1/2019 |
| FR | 2323436 | 4/1977 |
| FR | 2714985 | 7/1995 |
| FR | 2768211 | 3/1999 |
| FR | 2873777 | 10/2008 |
| GB | 707616 | 4/1954 |
| GB | 772888 | 4/1957 |
| GB | 1345442 | 1/1974 |
| GB | 1407408 | 9/1975 |
| GB | 1556492 | 11/1979 |
| GB | 2177006 | 1/1987 |
| JP | 5146648 | 4/1976 |
| JP | 52129004 | 10/1977 |
| JP | 5388205 | 8/1978 |
| JP | 6047899 | 3/1985 |
| JP | H0427867 | 1/1992 |
| JP | 7145795 | 6/1995 |
| JP | H08128609 | 5/1996 |
| JP | 2626991 | 7/1997 |
| JP | 11-000398 | 1/1999 |
| JP | 3049251 | 6/2000 |
| JP | 2000/337670 | 12/2000 |
| JP | 2001/160102 | 6/2001 |
| JP | 2002/206498 | 7/2002 |
| JP | 2002/253672 | 9/2002 |
| JP | 2002/306601 | 10/2002 |
| JP | 2003/023281 | 1/2003 |
| JP | 2004/019635 | 1/2004 |
| JP | 3488126 | 1/2004 |
| JP | 2004/524088 | 8/2004 |
| JP | 2005/051468 | 2/2005 |
| JP | 2005/134001 | 5/2006 |
| JP | 2006/283689 | 10/2006 |
| JP | 4066117 | 3/2008 |
| JP | 2008/073212 | 4/2008 |
| JP | 4358965 | 11/2009 |
| JP | 4659389 | 3/2011 |
| JP | 4760583 | 8/2011 |
| JP | 4865630 | 1/2012 |
| JP | 4909405 | 4/2012 |
| JP | 4993862 | 8/2012 |
| JP | 5410963 | 2/2014 |
| KR | 20060089125 | 8/2006 |
| KR | 101021827 | 1/2009 |
| NZ | 503495 | 3/2001 |
| NZ | 571421 | 4/2010 |
| SE | 527820 | 6/2006 |
| SE | 529989 | 1/2008 |
| WO | WO 1982/003548 | 10/1982 |
| WO | WO 93/05451 | 3/1993 |
| WO | WO 95/15778 | 6/1995 |
| WO | WO 97/32619 | 9/1997 |
| WO | WO 98/04311 | 2/1998 |
| WO | WO 1998/04311 | 2/1998 |
| WO | WO 98/31937 | 7/1998 |
| WO | WO 98/33433 | 8/1998 |
| WO | WO 98/57691 | 12/1998 |
| WO | WO 1998/57691 | 12/1998 |
| WO | WO 99/13932 | 3/1999 |
| WO | WO 99/22794 | 5/1999 |
| WO | WO 99/64747 | 12/1999 |
| WO | WO 00/13751 | 3/2000 |
| WO | WO 00/21602 | 4/2000 |
| WO | WO 00/27457 | 5/2000 |
| WO | WO 00/32261 | 6/2000 |
| WO | WO 00/50122 | 8/2000 |
| WO | WO 01/10489 | 2/2001 |
| WO | WO 01/32069 | 5/2001 |
| WO | WO 01/041854 | 6/2001 |
| WO | WO 01/73653 | 10/2001 |
| WO | WO 02/02169 | 1/2002 |
| WO | WO 2002/047749 | 6/2002 |
| WO | WO 02/066106 | 8/2002 |
| WO | WO 02/066107 | 8/2002 |
| WO | WO 03/066145 | 8/2003 |
| WO | WO 2004/020031 | 3/2004 |
| WO | WO 2004/022147 | 3/2004 |
| WO | WO 2004/041341 | 5/2004 |
| WO | WO 2004/041342 | 5/2004 |
| WO | WO 2004/073778 | 9/2004 |
| WO | WO 2005/011556 | 2/2005 |
| WO | WO 2005/021075 | 3/2005 |
| WO | WO 2005/051468 | 6/2005 |
| WO | WO 2005/079726 | 9/2005 |
| WO | WO 2005/123166 | 12/2005 |
| WO | WO 2006/000046 | 1/2006 |
| WO | WO 2006/074515 | 7/2006 |
| WO | WO 2006/096450 | 9/2006 |
| WO | WO 2006/126900 | 11/2006 |
| WO | WO 2006/130903 | 12/2006 |
| WO | WO 2007/006089 | 1/2007 |
| WO | WO 2007/014088 | 2/2007 |
| WO | WO 2007/019628 | 2/2007 |
| WO | WO 2007/033347 | 3/2007 |
| WO | WO 2007/045008 | 4/2007 |
| WO | WO 2007/045017 | 4/2007 |
| WO | WO 2007/048174 | 5/2007 |
| WO | WO 2007/048205 | 5/2007 |
| WO | WO 2007/048206 | 5/2007 |
| WO | WO 2007/064750 | 6/2007 |
| WO | WO 2007/103715 | 9/2007 |
| WO | WO 2007/140478 | 12/2007 |
| WO | WO 2007/143535 | 12/2007 |
| WO | WO 2007/147088 | 12/2007 |
| WO | WO 2008/007985 | 1/2008 |
| WO | WO 2008/030592 | 3/2008 |
| WO | WO 2008/030831 | 3/2008 |
| WO | WO 2008/060295 | 5/2008 |
| WO | WO 2008/068966 | 6/2008 |
| WO | WO 2008/076230 | 6/2008 |
| WO | WO 2008/091164 | 7/2008 |
| WO | WO 2008/096307 | 8/2008 |
| WO | WO 2008/102216 | 8/2008 |
| WO | PCT/AU2008/906390 | 12/2008 |
| WO | PCT/AU2009/900327 | 1/2009 |
| WO | WO 2009/026627 | 3/2009 |
| WO | WO 2009/052560 | 4/2009 |
| WO | WO 2009/059353 | 5/2009 |
| WO | WO 2009/064202 | 5/2009 |
| WO | PCT/AU2009/902731 | 6/2009 |
| WO | PCT/AU2009/904236 | 9/2009 |
| WO | WO 2009/124198 | 10/2009 |
| WO | WO 2009/132753 | 11/2009 |
| WO | WO 2009/146484 | 12/2009 |
| WO | WO 2009/156921 | 12/2009 |
| WO | WO 2010/066004 | 6/2010 |
| WO | WO 2010/092496 | 8/2010 |
| WO | WO 2011/068418 | 6/2011 |
| WO | WO 2011/078703 | 6/2011 |
| WO | WO 2012/164407 | 12/2012 |
| WO | WO 2015/020540 | 2/2015 |

OTHER PUBLICATIONS

Correspondence regarding FDA 510(k) submission, exhibit 1025 in case No. IPR2016-01727 dated Aug. 6, 1997, 5 pages.

Counterstatement In the Matter of Patents Act 1953 and In the Matter of New Zealand Patent Application No. 589990 in the name of ResMed Limited (The Applicant) and In the Matter of an Opposition thereto by Fisher & Paykel Healthcare Limited {The Opponent), Dec. 20, 2013.

Decision of the Assistant Commissioner—Opposition to NZ patent application No. 589990 dated Aug. 22, 2017, (Aug. 22, 2017), pp. 1-29.

(56) References Cited

OTHER PUBLICATIONS

Exhibit PP001—Evidence of Prior Publication in New Zealand regarding D1-D8, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Nov. 24, 2014.
Exhibit ST01—Statutory Declaration of Stainslav Tatkov, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Dated Nov. 24, 2014.
Extended European Search Report for Application No. 16162737.7 dated Jun. 29, 2016.
First Amended Statement of Case, In the Matter of Patents Act 1953 and In the Matter of New Zealand Patent Application No. 589990 in the name of ResMed Limited and In the Matter of an Opposition thereto by Fisher & Paykel Healthcare Limited under Section 21, Nov. 25, 2014.
Flexifit instructions, http://web.archive.org/web/1 9970126045828/ http:/www.archive.org/ dated Jan. 26, 1997, Affidavit of Christopher Butler dated Sep. 6, 2016, 23 pages.
Guidelines for Sandwich Core Materials, http://fibreglast.com/ product/guidelines-for-sandwich-core-materials/Learning_Center, dated Oct. 5, 2015, 3 pages.
HC200 Series Nasal CPAP Blower and Heated Humidifier Fisher & Paykel Healthcare, 17 pages.
International Search Report for PCT/EP2009/002532 dated Jul. 13, 2009.
International Search Report, PCT/AU09/00671, dated Sep. 9, 2009.
Malloy, Plastic Part Design for Injection Molding, New York: Hanser Publishers, 1994, 14 pages.
McGinley, Brian, M., et al., A Nasal Cannula Can Be Used To Treat Obstructive Sleep Apnea, Am J Respir Grit Care Med, vol. 176, pp. 194-200,2007.
Opus Brochure, Fisher & Paykel Healthcare, www.fphcare.com, 2 pages.
Patents Form No. 15, "First Amended Notice of Opposition to Grant of Patent {Section 21 )", Oct. 22, 2013.
ResMed Mask Frames, Nasal Cushions and Headgear, http://web. archive.org/web/19970 1 26045828 /http ://www.a rchive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask—Component Cards, www.resmed. com Reference No. 1010279/30502, dated 2005, 1 page.
ResMed Origins Brochure dated Apr. 17, 2016, 64 pages.
SleepStyle600 CPAP Series Operating Manual, Thermo Smart, www.Manualslib.com, Fisher & Paykel Healthcare, 11 Pages.
Sreenan, MB, Con, et al., High-Flow Nasal Cannulae in the Management of Apnea of Prematurity: A Comparison with Conventional Nasal Continuous Positive Airway Pressure, Pediatrics, vol. 107, No. 5, May 2001.
Statement of Case In the Matter of Patents Act 1953 and In the Matter of New Zealand Patent Application No. 589990 in the name of ResMed Limited and In the Matter of an Opposition thereto by Fisher & Paykel Healthcare Limited under Section 21, Dated Oct. 22, 2013.
Statutory Declaration of Professor Alan Richard Schwartz in Support of New Zealand Patent Application No. 589990 dated May 23, 2016, 64 pages with Exhibits.
Statutory Declaration of Professor Jason Paul Kirkness in Support of New Zealand Patent Application No. 589990 dated May 23, 2016, 49 pages with Exhibits.
Stuff.co.nz, Sleeping beautifully article, exhibit 1024 in case No. IPR2016-01730 dated Dec. 17, 2013, 4 pages.
Sullivan HumidAire User's Instructions, exhibit 1027 in case No. IPR2016-01727, 8 pages.

Third Amended Counterstatement in the Matter of Patents Act 1953 and In the Matter of New Zealand Patent Application No. 589990 in the name of ResMed Limited (The Application) and In the Matter of an Opposition thereto by Fisher & Paykel Healthcare Limited (The Opponent), May 27, 2016, 11 pp.
TN1a20 Treatment with Nasal lnsufflation, Product Information, Seleon GmbH,seleon@seleon.de,www.seleon.de.
U.S. Appl. No. 61/058,659, filed Jun. 4, 2008.
Ultra Mirage Full Face Mask brochure, http://web.archive.org/web/ 19970 1 26045828/http://www.archive.org/ dated Jan. 26, 1997, Affidavit of Christopher Butler dated Sep. 6, 2016, 9 pages.
Users Guide ResMed Mirage Swift Nasal Pillows System, www. myresmed.com dated May 6, 2004, 11 pages.
Apex Medical Corporation, Petition Exhibit 1002 in IPR2014-00551, "ResMed's First Amended Complaint for Patent Infringement—Jury Trial Demanded", Case No. SACV-13-00498 CJC (RNBx), USDC, Central District of California, Southern Division, 18 pages.
Breas Medical AB "iSleep® 20" Brochure, Dec. 2007, 2 pages.
Communication dated Jul. 1, 2010 in European Appln. No. 02 700 014.0 (5 pages).
Communication Pursuant to Article 94(3) EPC (examination report) dated Jun. 12, 2015 in European Application No. 02 700 014.0 (3 pages).
Communication Pursuant to Article 94(3) EPC (examination report) dated Jun. 5, 2015 in European Application No. 10 189 422.8 (4 pages).
Communication Pursuant to Article 94(3) EPC (European Examination Report) dated Oct. 7, 2015 in EP Application No. 12 159 042.6 (4 pages).
Communication Pursuant to Article 94(3) EPC dated Feb. 4, 2015 in European Application No. 12 159 042.6 (4 pages).
Complaint for Patent Infringement—Jury Trial Demanded as filed in the United States District Court, Southern District of California, Case No. '13CV1246 MMAWMC, dated May 31, 2013, 18 pages.
ITC Action related to Certain Sleep-Disordered Breathing Treatment Systems and Components Thereof, Inv. No. 337-TA- , CBI 13-185, filed on Mar. 28, 2013, 57 pages.
ResMed's First Amended Complaint for Patent Infringement, filed in the United States District Court Central District of California Southern Division, filed on Apr. 8, 2013, 342 pages.
De Vilbiss® Healthcare, "DeVilbiss IntelliPAP® Standard CPAP System," Nov. 2007, 2 pages.
Declaration of Joseph Dyro, Petition Exhibit 1007.
Examination Report dated Oct. 10, 2003 in New Zealand Appln. No. 527088 (2 pages).
Extended European Search Report dated Apr. 28, 2011 in European Appln. No. 10189422.8 (5 pages).
Extended European Search Report dated May 4, 2012 in European Appln. No. 12159042.6 (5 pages).
Final Notice of Reasons for Rejection delivered Sep. 24, 2008 in Japanese Appln. No. 2002-565664, with English translation (6 pages).
Fischer & Paykel, "Two Easy Steps to Comfort", 4 pages, Aug. 1995.
Fisher & Paykel Healthcare "SleepStyle™ 200 CPAP Series" Specification Sheet, 1998, 4 pages.
Fisher & Paykel Healthcare "SleepStyle™ 200 CPAP Series" Specification Sheet, 2005, 4 pages.
Fisher & Paykel Healthcare "SleepStyle™ 600 CPAP Series" Specification Sheet, 2005, 4 pages.
Fisher & Paykel Healthcare Two Easy Steps to Comfort, Humidification and Nasal CPAP Therapy, Aug. 1995, 4 pages.
Fisher & Paykel Healthcare, "HC200 Series Nasal CPAP Blower & Heated Humidifier User's Manual", 1998, 17 pages.
Fisher & Paykel Limited, New Zealand Application No. 503495, filed Mar. 21, 2000, 29 pages.
German Patent Manual for Hoffrichter/Sandmann CPAP Respirator—Perfect CPAP Therapy, 30 pages plus Translation Verification Certificate, Mar. 1998.
Hoffrichter "Vector CP AP—Therapy With Technical Mastery", 4 pages, Oct. 1998.
Hoffrichter GmbH "Vector therapy in perfection" Brochure, 2002, 2 pages.

(56) References Cited

OTHER PUBLICATIONS

International Preliminary Examination Report completed Oct. 4, 2002 in International Appln. No. PCT/AU02/00155 (3 pages).
International Search Report dated Mar. 21, 2002 in International Appln. No. PCT/AU02/00155 (2 pages).
J. H. Emerson Co., Cough Assist, "Non-Invasive Removal of Bronchial Secretions," 2 pages.
Madaus Schwarzer Medizintechnik, "New Approaches in Diagnosis and Therapy‡Moritz biLevel User Manual", May 1994, 38 pages.
Madaus Schwarzer Medizintechnik, "New Approaches in Diagnosis and Therapy—Max nCPAP User Manual", Mar. 1994, 38 pages.
Map Medizintechnik fuer Arzt and Patient "max II nCPAP moritz II biLevel—The gentle therapy for sleep-related breathing disorders" Brochure, 2000, 4 pages.
Map Medizintechnik, "minni Max nCPAP®" brochure, 12 pages, Mar. 2005.
Map Medizintechnik, "Moritz II biLEVEL®—The gentle therapy for sleep-related breathing disorders" brochure, 6 pages, Jan. 2001.
Map Medizin-Technologie GmbH "minni Max nCPAP®, The respiratory therapy device with• out an integrated humidifier", Dec. 2003, 17 pages.
Map Medizin-Technologie GmbH, Moritz®S/Moritz®ST—Sailing toward therapeutic success, Jul. 2004, 4 pages.
Microfilm of Japanese Utility-Model Application No. S54-003858 (Japanese Utility-Model Application Publication No. S55-104925).
Motion to Amend the Complaint and Notice of Investigation as filed in the United States International Trade Commission, Investigation No. 337-TA-879, dated May 31, 2013, 18 pages.
Notification of Acceptance of Request for Invalidation and English Translation for corresponding Chinese Patent No. 02804936.5, dated Mar. 20, 2014, 188 pages.
Notification of Acceptance of Request for Invalidation, Issued: Dec. 24, 2014, in Chinese Patent No. 02804936.5, with English translation, 62 pages.
Notification of Reasons for Rejection dated Feb. 19, 2008 in Japanese Appln. No. 2002-565664, with English translation (5 pages).
Notification of Second Office Action dated Jan. 27, 2006 in Chinese Appln. No. 02804936.5, with English Translation (6 pages).
Notification of the First Office Action dated Jul. 22, 2005 in Chinese Appln. No. 02804936.5, with English translation (8 pages).
Office Action dated Jan. 22, 2008 in Japanese Patent Appln. No. 2002-565665 (w/English translation) (12 pages).
Patent Owner Exhibit No. 2001 in IPR2014-00551, Applicant Transmittal to USPTO re Completion of National Phase Filing of the PCT Application for the Mayer Reference, Aug. 6, 2002, 4 pages.
Patent Owner Exhibit No. 2002 in IPR2014-00551, RE44,453 Patent Application Data Sheet, Initial May 4, 2011 5 pages.
Patent Owner Exhibit No. 2003 in IPR2014-00551, Decision of the Patent Trial and Appeal Board Denying Institution of Inter Partes Review of U.S. Pat. No. 7,614,398, entered Feb. 20, 2014, 5 pages.
Patent Owner Exhibit No. 2005 in IPR2014-00551, U.S. National Stage Worksheet of USPTO re National Phase Requirements Completion for the Mayer Reference, 1 page.
Patent Owner Exhibit No. 2010 in IPR2014-00551, Deposition Transcript of Dr. Joseph F. Dyro in Connection with Inter Partes Review Proceedings IPR2013- 00511, IPR2013-00512, IPR2013-00514, IPR2013-00515, and IPR2013-00516, Apr. 21, 2014, 46 pages.
Patent Owner Exhibit No. 2011 in IPR2014-00551, Patent Owner ResMed Limited's Preliminary Response to Apex Medical Corp.'s Petition for Inter Partes Review of U.S. Pat. No. 7,614,398, Case No. IPR2013-00513, Nov. 22, 2013, 15 pages.
Petition Exhibit 1003 in IPR2014-01 196, REMStar® Heated Humidifier Manual, Mar. 15, 2001, 8 pages.
Petition Exhibit 1004 in IPR2014-01363, Declaration of Steve Bordewick, Aug. 22, 2014, 90 pages.
Petition Exhibit 1004 in IPR2014-01 196, Declaration of Steve Bordewick, Jul. 22, 2014, 59 pages.
Petition Exhibit 1006 in IPR2014-00551, Patent Owner Amendment mailed Mar. 27, 2009, in U.S. Appl. No. 11/181,807, 10 pages.
Petition Exhibit 1006 in IPR2014-01 196, Patent Owner ResMed Limited's Preliminary Response filed Jul. 10, 2014, in IPR2014-00551, 41 pages.
Petition Exhibit 1007 in IPR2014-00551, Declaration of Joseph Dyro in Support of Inter Partes Review of U.S. Patent RE44,453, executed Mar. 26, 2014, 15 pages.
Petition Exhibit 1007 in IPR2014-01 196, ITC Investigation No. 337-TA-890,: Order No. 7: Initial Determination Granting Complainants' Motion to Amend Complaint and Notice of investigation and Granting Respondents' Motion to Terminate the Investigation with Respect to U.S. Pat. No. 7,614,398, served Feb. 4, 2014, 8 pages.
Petition Exhibit 1008 in IPR2014-01 196, Case No. 13-cv-1246-CAB (WMc), Order on Motion to Stay, Motion to Dismiss, and Related Discovery Request, Oct. 15, 2013, 3 pages.
Petition Exhibit 1009 in IPR2014-01 196, Case No. SACV 13-00498: Order Granting Defendants' Motion to Stay Litigation Pending Inter Partes Review, Oct. 4, 2013, 3 pages.
Petition Exhibit 1010 in IPR2014-01 196: Patent Prosecution History of Reissue U.S. Appl. No. 13/944,960, filed Jul. 18, 2013, 228 pages.
Petition Exhibit 1011 in IPR2014-01 196: Patent Prosecution History of U.S. Pat. No. 7,614,398, 174 pages.
Petition Exhibit No. 1012 in IPR2014-01 196: Patent Prosecution History of U.S. Pat. No. RE44,453, 2157 pages.
Petition Exhibit No. 1013 in IPR2014-01 196: Proof of Service of 3B Medical, Inc. in Civil Action No. 13-cv-1246-MMA-WMC, 5 pages.
Petition Exhibit No. 1014 in IPR2014-01 196: Australian Application No. PR 3117, filed Feb. 16, 2001, 17 pages.
Petition Exhibit No. 1015 in IPR2014-01196: ITC Investigation No. 337-TA-890: Order No. 8: Construing Terms of the Asserted Patents, served Jan. 17, 2014, 51 pages.
Petition Exhibit No. 1016 in IPR2014-01196: ITC Investigation No. 337-TA-890: Order No. 14: Denying Respondents' Motion for Summary Determination of Invalidity of U.S. Pat. No. RE44,453, served Mar. 26, 2014, 19 pages.
Petition Exhibit No. 1020 in IPR2014-01 196: Australian Application No. PR 7288, filed Aug. 27, 2001, 23 pages.
Petition Exhibit No. 1022 in IPR2014-01196: ITC Investigation No. 33 7-T A-890: Notice of Commission Determination Not to Review an Initial Determination Granting the Complainants' Motion to Amend the Complaint and Notice of Investigation to Substitute U.S. Pat. No. RE44,453 for U.S. Pat. No. 7,614,398 and Granting Respondents' Motion to Terminate the Investigation with Respect to U.S. Pat. No. 7,614,398, Issued: Feb. 10, 2014, 3 pages.
Petition for Inter Partes Review of U.S. Pat. No. 7,614,398, mailed on Aug. 16, 2013.
Petition for Inter Parties Review of U.S. Pat. No. Re 44,453, *BMC Medical Co. Ltd.*, Petitioner v. *ResMed Limited*, Patent Owner, Case No. IPR2014-01363, Aug. 22, 2014, 66 pages.
Petition for Inter Parties Review of U.S. Pat. No. RE44,453 Under to 35 U.S.C. §§ 311 ET Seq. and 37 C.F.R. §42.100 ET Seq., *Apex Medical Corp.*, Petitioner v. *ResMed Limited*, Patent Owner, Case No. IPR2014-00551, Mar. 27, 2014, 38 pages.
Petition for Inter Parties Review of U.S. Patent No. RE44,453 Under to 35 U.S.C. §§311-319 and 37 C.F.R. §42.100 et seq., *BMC Medical Co. Ltd.*, Petitioner v, *ResMed Limited*, Patent Owner, Case No. IPR2014-01 196, Jul. 23, 2014, 62 pages.
Photos of HumidAire™, 11 pages.
Photos of MAP Humidifier and Tub, 2 pages and cover sheet, undated.
Photos of tray system available before the critical date, with sample flow generator and humidifier, 5 pages.
ResMed "Sullivan® HumidAire® User's Instructions", 8 pages, 1998.
ResMed, "The Sullivan® HumidAire™", 1997, 1 page.
Respironics "System One Heated Humidifier User Manual", May 2009, 20 pages.

(56) References Cited

OTHER PUBLICATIONS

Supplementary European Search Report dated Sep. 15, 2009 in European Appln. No. 02700014.0, (3 pages).
U.S. International Trade Commission, Inv. No. 337-TA-890, "Notice of the Commission's Final Determination; Issuance of a Limited Exclusion Order and Cease and Desist Orders; Termination of the Investigation," Issued Dec. 23, 2014, 25 pages.
U.S. International Trade Commission, Inv. No. 337-TA-890, "Office of Unfair Import Investigations' Petition for Review of the Initial Determination," dated Nov. 7, 2014 (Public Version Filed: Dec. 3, 2014), 5 pages.
U.S. International Trade Commission, Inv. No. 337-TA-890, "Office of Unfair Import Investigations' Petition for Review of the Initial Determination," dated Sep. 11, 2014 (Public Version Filed: Oct. 8, 2014), 37 pages.
U.S. International Trade Commission, Inv. No. 337-TA-890, "Office of Unfair Import Investigations' Petition for Review of the Initial Determination," dated Sep. 3, 2014 (Public Version Filed: Oct. 8, 2014), 34 pages.
U.S. Patent and Trademark Office, Case IPR2014-01196 and IPR2014-01363, U.S. Pat. No. RE 44,453 E, "Scheduling Order," Entered: Jan. 21, 2015, 9 pages.
U.S. Patent and Trademark Office, Case IPR2014-01196, U.S. Pat. No. RE 44,453 E, "Decision Institution of Inter Partes Review 37 C.F.R. §42.108," Paper No. 7, Entered Dec. 21, 2014, 11 pages.
United States Patent and Trademark Office, Before the Patent Trial and Appeal Board, *BMC Medical Co., Ltd., 3B Products, L.L.C. and 3B Medical Inc.* (Petitioner) v. *ResMed Limited* (Patent Owner), Final Written Decision, Paper 25, Entered Jan. 19, 2016 in IPR2014-01196 (14 pages).
United States Patent and Trademark Office, Before the Patent Trial and Appeal Board, *BMC Medical Co., Ltd., 3B Products, L.L.C. and 3B Medical Inc.* (Petitioner) v. *ResMed Limited* (Patent Owner), Final Written Decision, Paper 25, Entered Jan. 20, 2016 in IPR2014-01363 (39 pages).
U.S. Patent and Trademark Office, Case IPR2014-01363, U.S. Pat. No. RE 44,453 E, Decision Institution of Inter Partes Review 37 C.F.R. §42.108, Paper No. 7, Entered: Jan. 21, 2015, 21 pages.

\* cited by examiner

TREATMENT OF RESPIRATORY CONDITIONS

CROSS-REFERENCE TO RELATED APPLICATIONS

This application is a continuation of U.S. patent application Ser. No. 16/258,176 filed Jan. 25, 2019, which is a continuation of U.S. patent application Ser. No. 12/995,561 filed Dec. 1, 2010, which is a 371 Application of PCT/AU2009/000671 filed May 28, 2009, which claims the benefit of the filing dates of U.S. Provisional Patent Application No. 61/059,084 filed Jun. 5, 2008 and U.S. Provisional Patent Application No. 61/117,375 filed Nov. 24, 2008, the disclosures of which are hereby incorporated herein by reference.

1. FIELD OF THE TECHNOLOGY

The present technology relates to methods and apparatus for treatment of respiratory conditions such as the conditions related to sleep disordered breathing (SDB) (including mild obstructive sleep apnea (OSA)), allergy induced upper airway obstruction or early viral infection of the upper airway.

2. BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with SDB are also likely to disturb their partner's sleep. One known effective form of treatment for patients with SDB is nasal continuous positive airway pressure (nasal CPAP) applied by a blower (air pump or compressor) via a connecting hose and patient interface. In some forms the supply of air at positive pressure is delivered to both the nose and mouth. The positive pressure can prevent a collapse of the patient's airway during inspiration, thus preventing events such as snoring, apnoeas or hypopnoeas and their sequelae.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly change with the patient's breathing cycle. A pressure setting during expiration lower than inspiration may generally be referred to as expiratory pressure relief. An automatically adjusting device may increase the treatment pressure in response to indications of partial or complete upper airway obstruction. See U.S. Pat. Nos. 5,245,995; 6,398,739; 6,635,021; 6,770,037; 7,004,908; 7,141,021; 6,363,933 and 5,704,345.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

It may be desirable to develop further methods and devices for treating upper respiratory conditions.

3. SUMMARY OF THE TECHNOLOGY

A first aspect of the some embodiments of the technology is to provide methods and apparatus for treatment of respiratory conditions.

Another aspect of some embodiments of the technology is to provide methods and apparatus for treating sleep disordered breathing.

In one embodiment of the technology, air at a high flow rate is delivered to the nasal passages, preferably in the range of about 10 to about 35 litres/minute.

In another embodiment, air is provided with a temperature in the range of about 30° C. to about 37° C.

In another embodiment, air with a high humidity is provided to the nasal passages, preferably with an absolute humidity in the range of about 27 to about 44 mg/litre.

In another embodiment, methods and apparatus are provided for servo-controlling sleep disordered breathing by varying one or more of flow, temperature and level of humidification.

Another aspect of the technology is to provide a device for treating respiratory conditions having one or more start-up and/or shut-down protocols that vary any of flow, temperature and level of humidification. For example, the device may provide for ramping any one or more of flow, temperature and level of humidification.

Another aspect of the technology is to vary any of flow, temperature and level of humidification within, or as a function of detection of, a respiratory cycle of a patient. For example, a device may provide first levels of flow, temperature and/or humidification during inhalation and second or different levels of flow, temperature and/or humidification during exhalation.

Another aspect of the technology is to provide different levels of flow, temperature and/or humidification to each naris. For example, in one form of device, levels of flow, temperature and/or humidification are cycled between the nares.

In accordance with the technology, methods and apparatus are provided for varying the levels of flow, temperature and/or humidification.

In accordance with the technology, levels of flow, temperature and/or humidification may be varied either manually or automatically.

In accordance with the technology, levels of one or more of flow, temperature and humidification may be varied over a period having a duration less than, equal to or greater than the duration of a respiratory cycle. For example, flow, temperature and humidification may be increased over several breaths, or decreased over several breaths.

Another aspect of the technology is to provide an air delivery conduit having a diameter that changes along its length.

Another aspect of the technology is to provide each naris with individually controlled levels of flow, temperature and/or humidity.

Additional features of the present respiratory technology will be apparent from a review of the following detailed discussion, drawings and claims.

4. BRIEF DESCRIPTION OF DRAWINGS

The present technology is illustrated by way of example, and not by way of limitation, in the figures of the accompanying drawings, in which like reference numerals refer to similar elements including:

FIGS. 16-19 schematically illustrate an interface system according to another sample embodiment of the invention.

Figure 20:
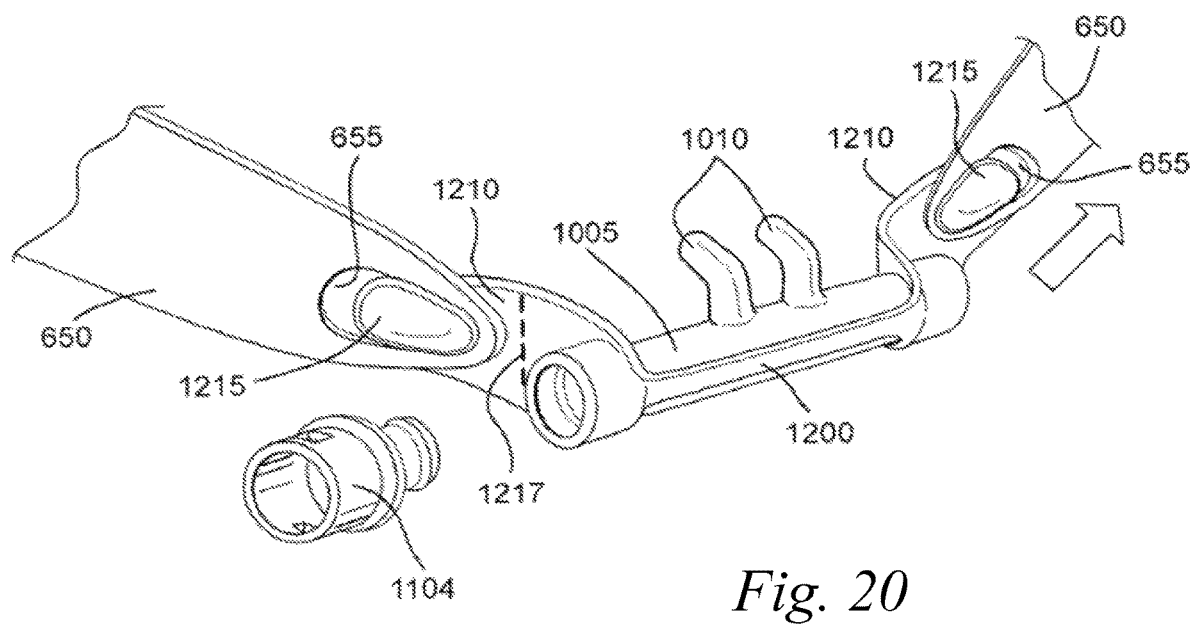
Figure 21:
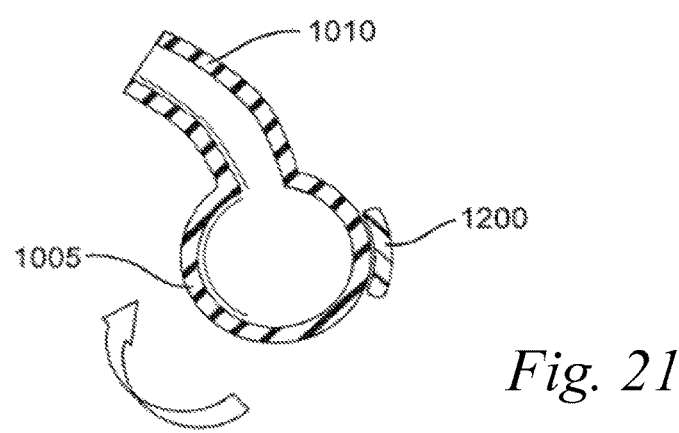

FIGS. 20 and 21 schematically illustrate an interface system according to another sample embodiment of the invention.

FIGS. 22a-22j schematically illustrate an interface system according to another sample embodiment of the invention.

5. DETAILED DESCRIPTION

Figure 1:
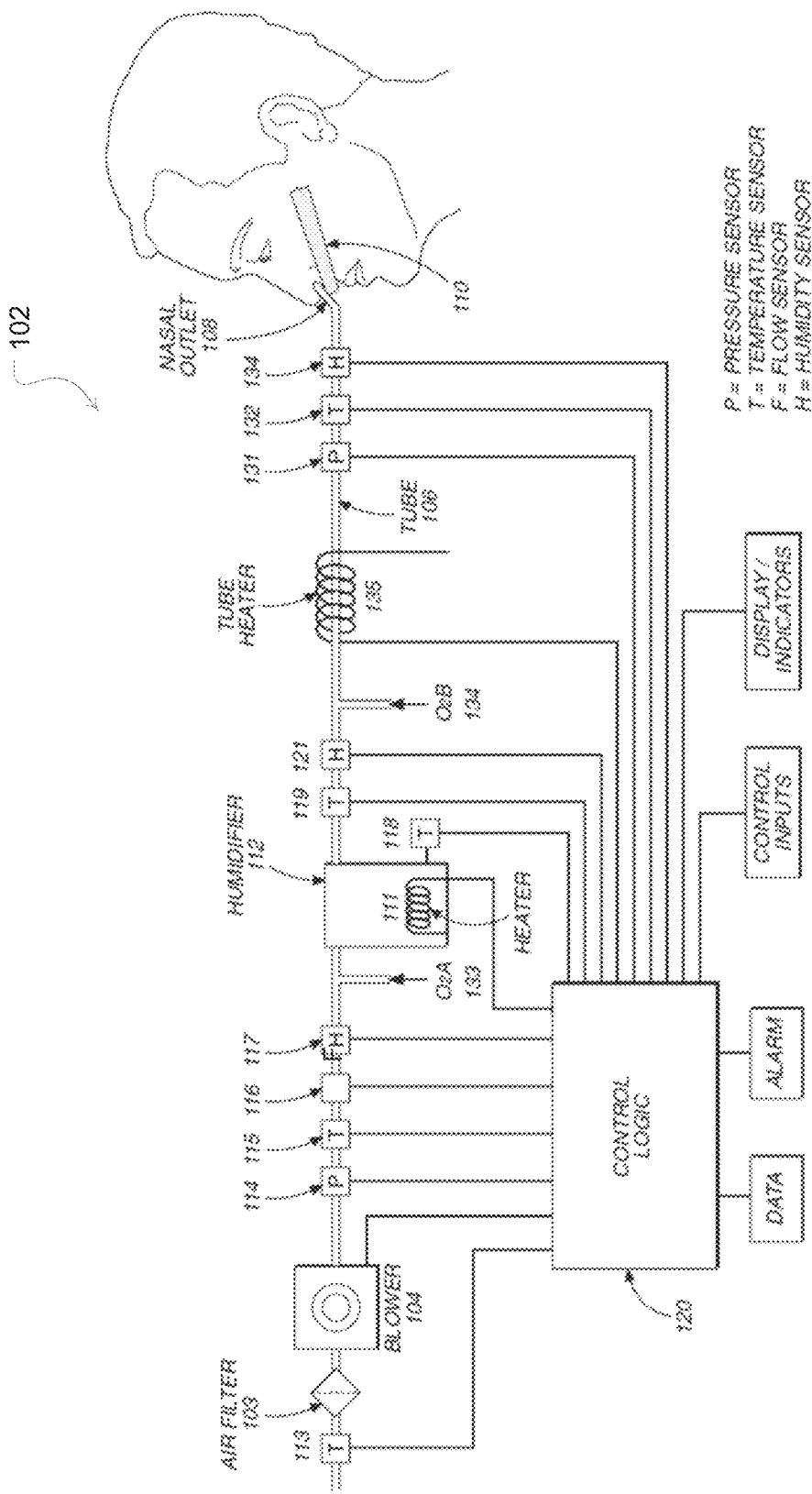
FIG. 1 shows example components of an apparatus for treatment of the upper airway of a patient.

The embodiments of the present technology may be implemented with an airway treatment device 102 that may include some or all of the components illustrated in FIG. 1. For example, the airway treatment delivery device will typically include a flow generator such as a servo-controlled blower 104. The blower 104 will typically include an air inlet and impeller driven by a motor (not shown). Optionally, the air inlet may be coupled with a gas supply, such as for oxygen as shown in FIG. 1, to mix with or supplement the breathable gas supplied by the impeller to the airway of a user. Optionally, the supplementary gas supply may be introduced through a port, 133, upstream of the humidifier, and/or downstream of the humidifier, through a port 134. Moreover, an air filter may be provided, such as a HEPA filter, to remove dust or other allergens from the air drawn into the air inlet. The blower may optionally be configured for generating varied flows or pressures.

The delivered breathable gas flow rate may be in the range of about −250 to about +250 liters/min, more preferably between about −100 and about 100 liters/min, more preferably, between about 0 to 100 liters/min, more preferably between about 0 and 75 liters/min, yet further more preferably between about 0 to about 50 liters/min with the preferred range being between about 10 to about 35 liters/min, to provide for comfort and efficacy.

The delivered breathable gas temperature may be in the range of about −10° C. to about 50° C., more preferably about +4° C. to about +45° C., yet more preferably room temperature up to 40° C. with the most preferred range being 30° C. to 37° C., to provide for comfort and efficacy.

The delivered breathable gas relative humidity may be in the range of room humidity up to 100%, for example in the range of about 50% to about 100%, or about 70% to about 100%, or about 80% to about 95%, with the preferred range being 90% to 100%, to provide for comfort and efficacy. An absolute humidity range will be about 0 to about 82 mg/liter, or more preferably about 27 to about 44 mg/liter.

5.1 Patient Interface

The airway treatment device 102 will also typically include a patient interface such as an air delivery conduit 106 and nasal prongs or nasal cannula 108 to carry the flow of air or breathable gas to the upper airway of a user of the device or patient. The blower 104 can be coupled with the air delivery conduit 106 and the nasal cannula 108 so as to provide the breathable gas from the blower 104. In one form of patient interface, as will be discussed in more detail with respect to the particular interface embodiments herein, exhaust gas of the blower and/or expiratory gas from the patient's airway can be vented away from the patient interface from a location proximate to the patient's airway or the nares themselves. Significant gaps or venting between the patient interface and the nares of the patient can permit a flow from the flow generator to escape or leak from the patient's nares without being inspired. A patient interface that permits such venting can provide a comfortable interface for the treatment described herein. Thus, a patient interface that provides a leak-free seal with the nares of the patient is not required. However, a sealed patient interface may be used as an alternative.

The patient interface will typically be held in place proximate or inside the nares of the patient. A harness 110 may be optionally provided for this purpose. In addition, a nasal or septum clip and/or adhesive (not shown) may also be provided to maintain the nasal cannula in a desired position for use. Examples of suitable embodiments of the patient interface are disclosed in U.S. Patent Provisional Patent Application No. 61/058,659, entitled "Unobtrusive Interface Systems," filed on Jun. 4, 2008, the disclosure of which is hereby incorporated herein by cross-reference. In some embodiments, the nasal cannula may also or alternatively include ear attachment portions connected with the nasal cannula to ensure positioning of nasal cannula by or in the nares during treatment. For example, cannula arms extending over and/or around the ears from the nasal cannula may be utilized. Optionally, the delivery conduit may be incorporated with such cannula arms, which may alternatively be designed to run under the ears rather than over the ears to reduce noise that might otherwise be heard by the user from the flow of gas through the delivery conduit.

Figure 22A:
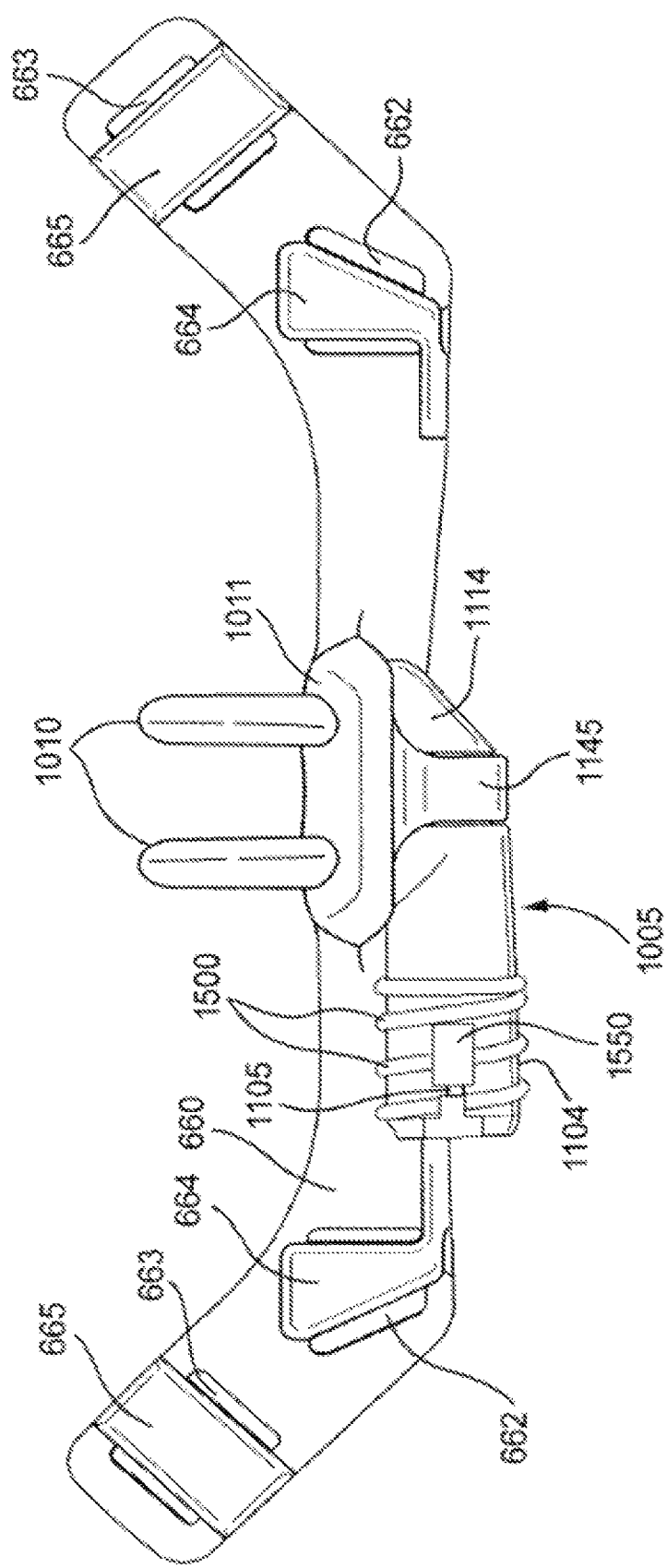
Figure 22B:
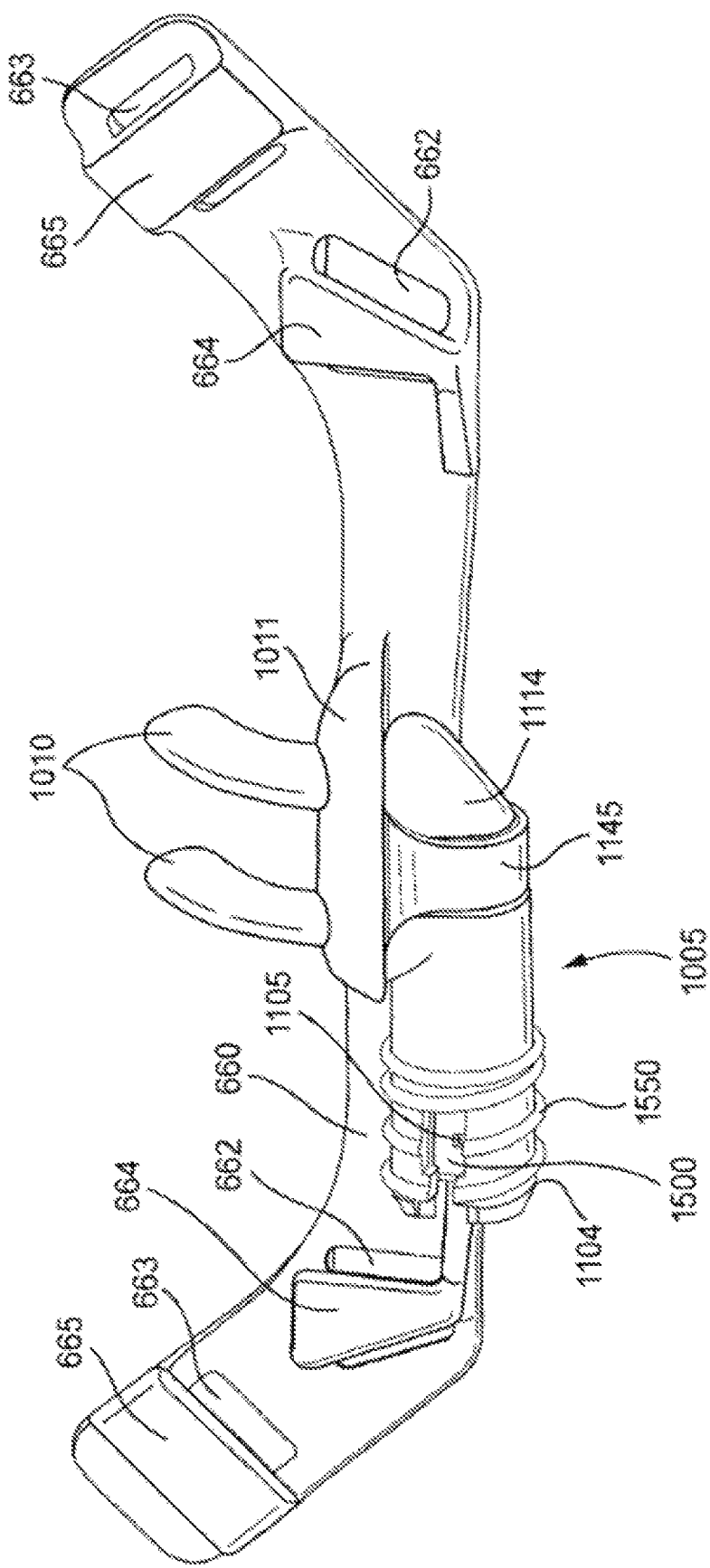
Figure 22C:
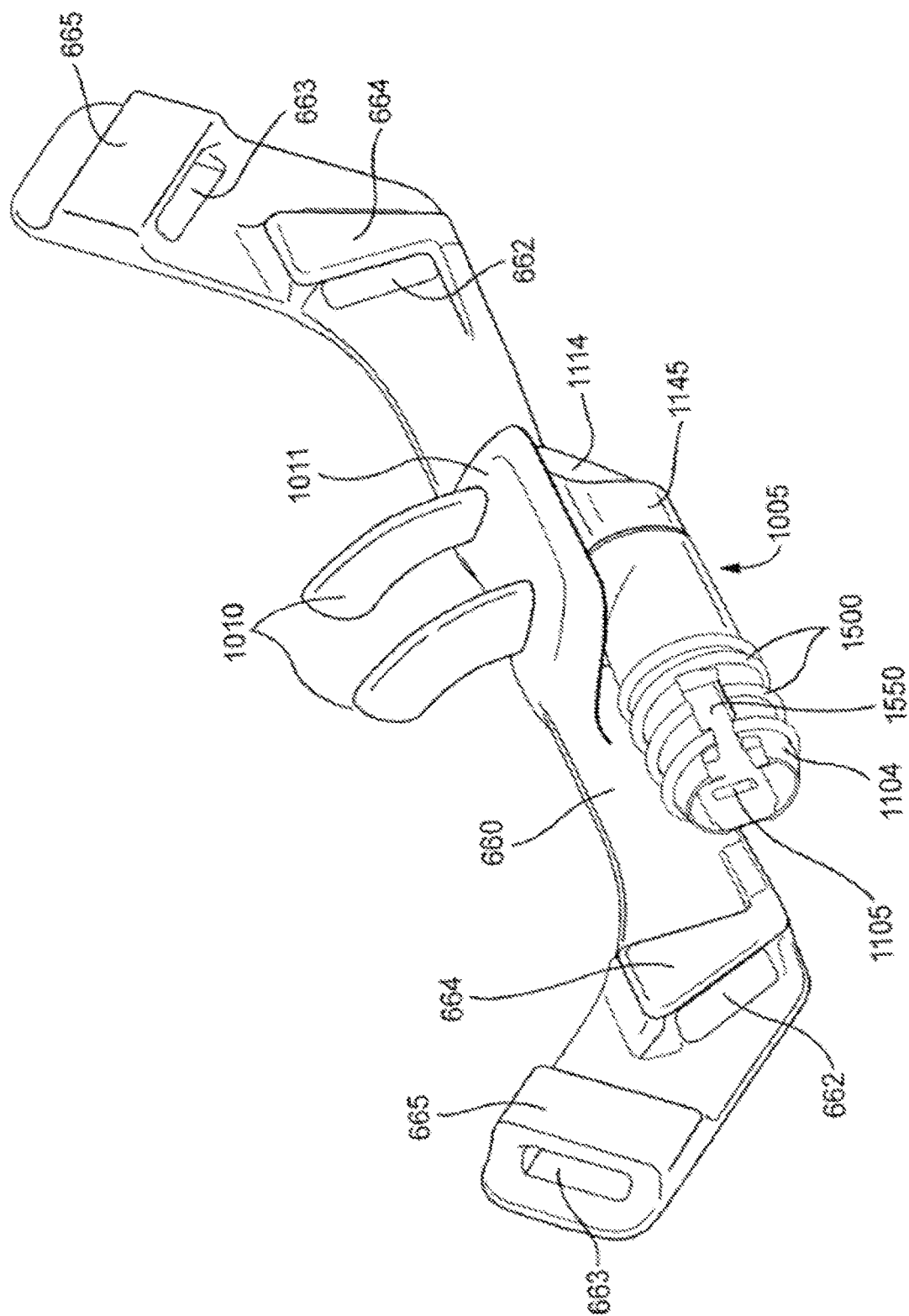
Figure 22D:
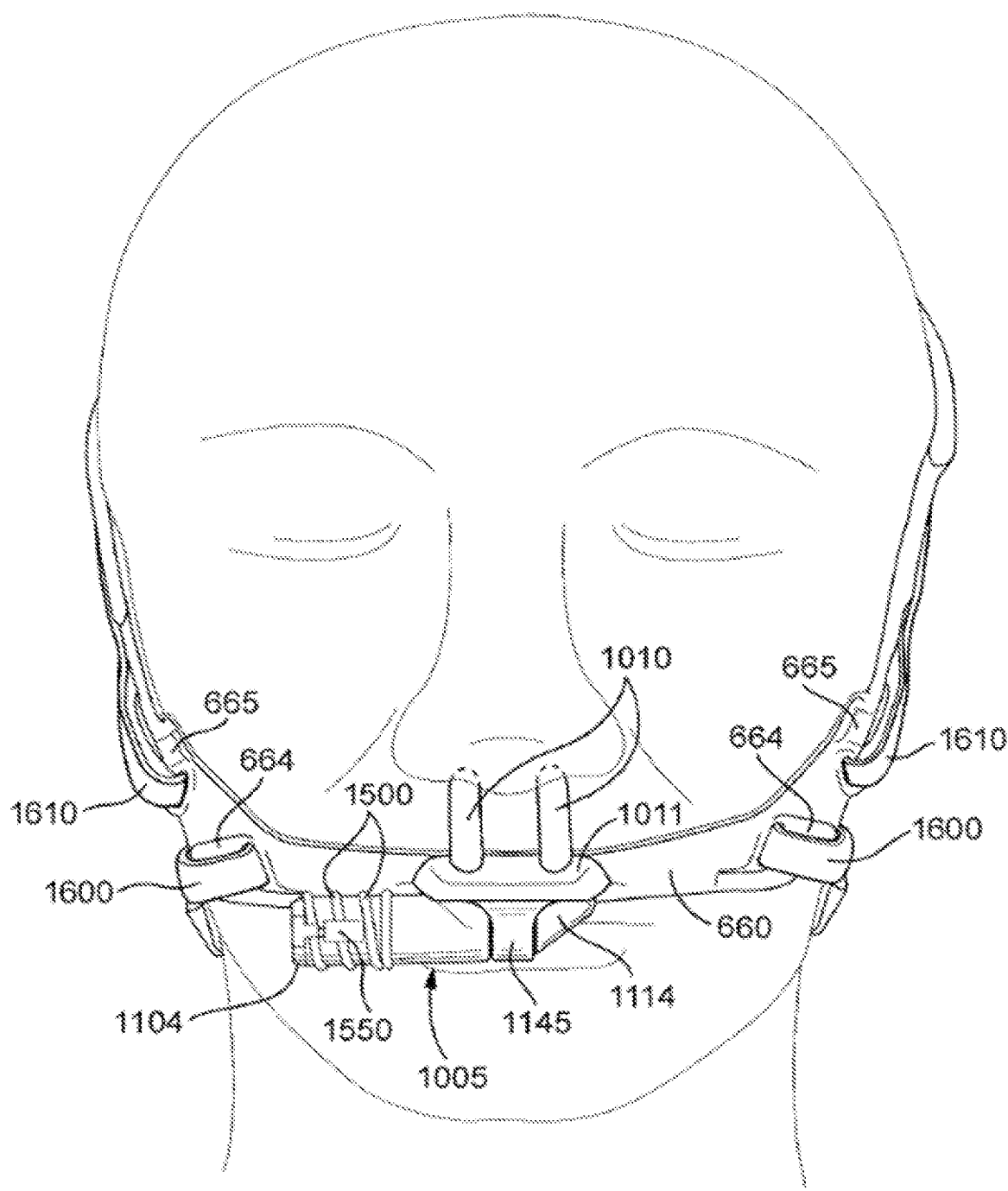
Figure 22E:
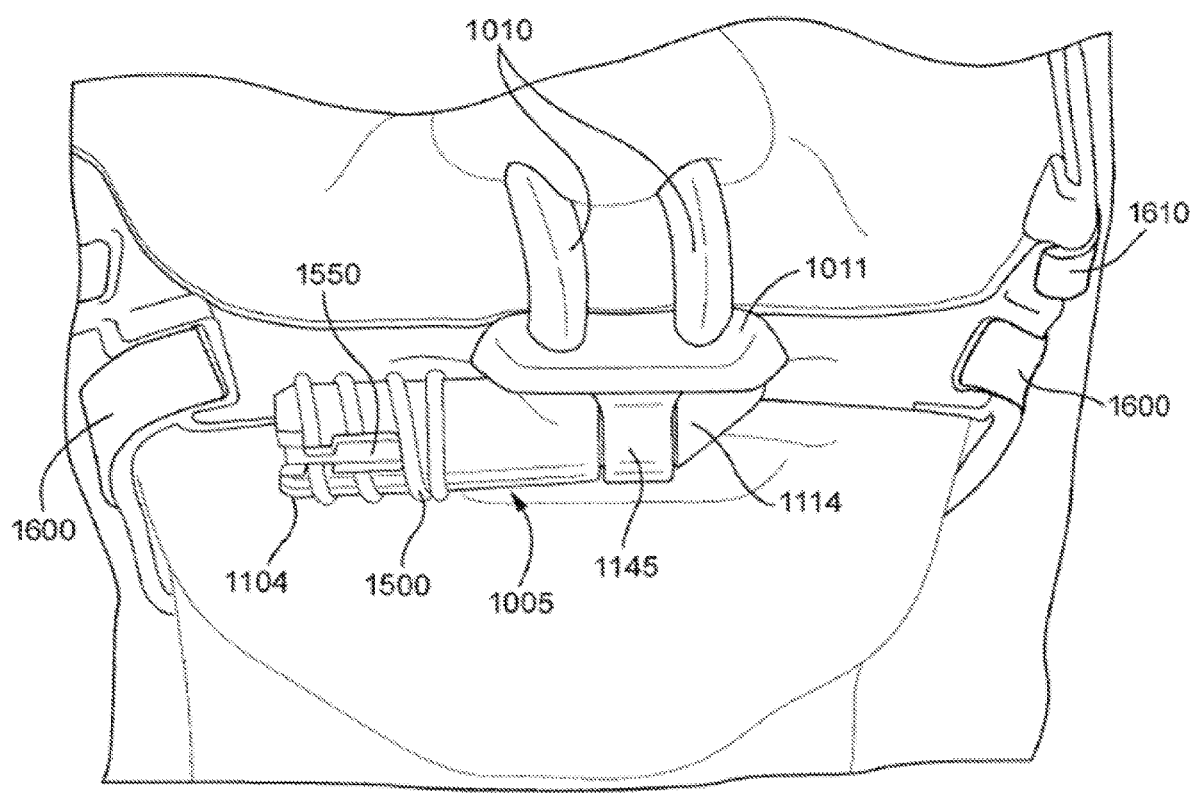
Figure 22F:
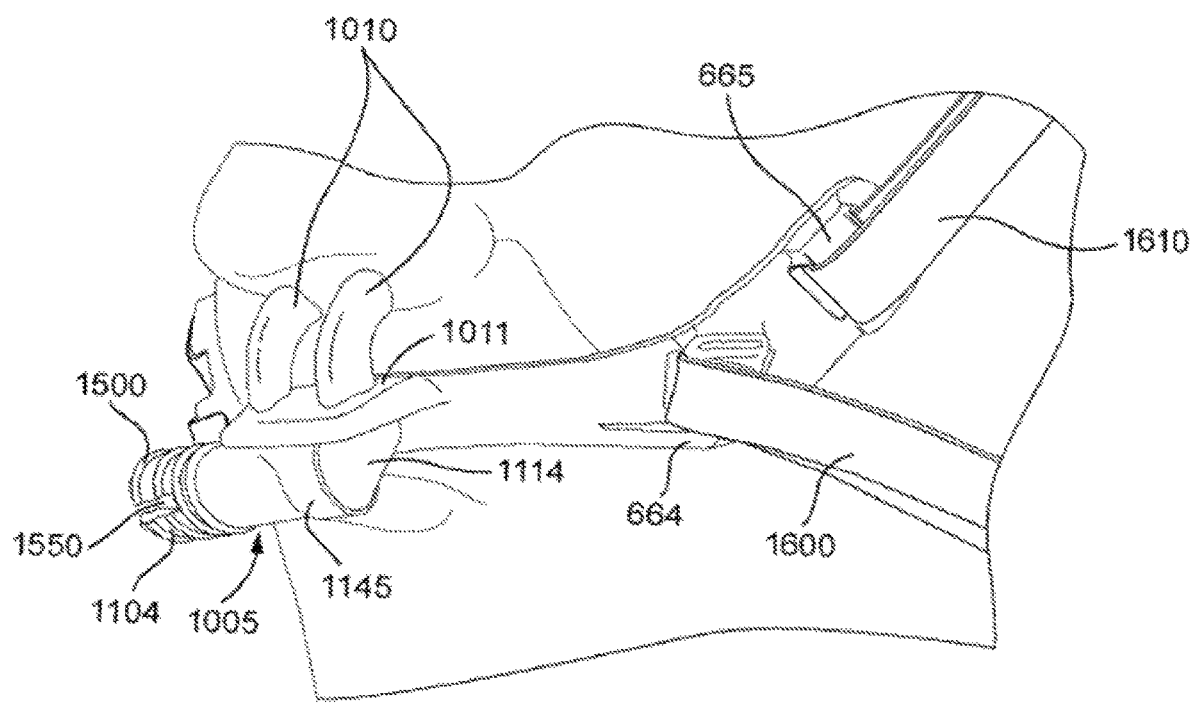
Figure 22G:
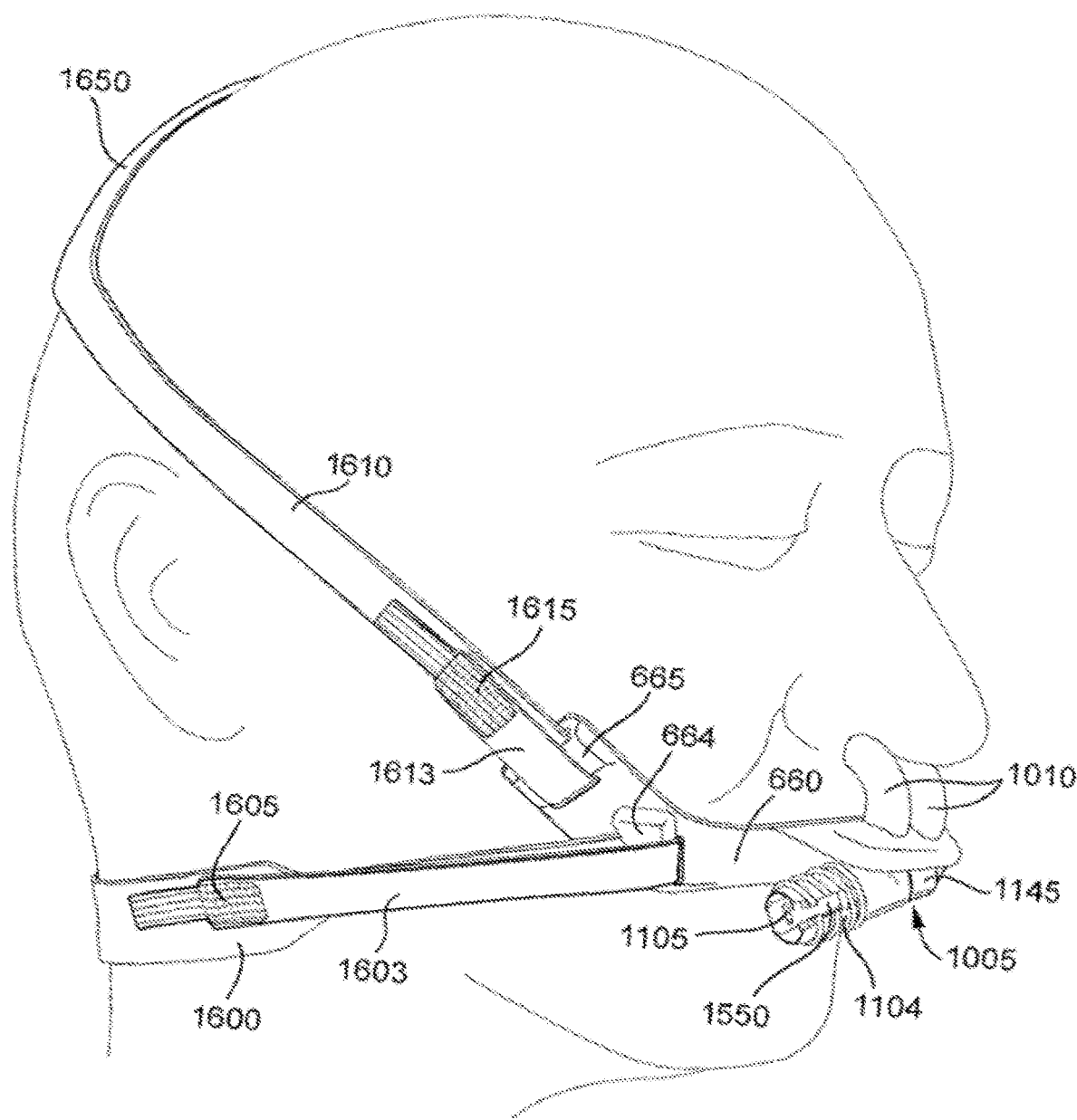
Figure 22H:
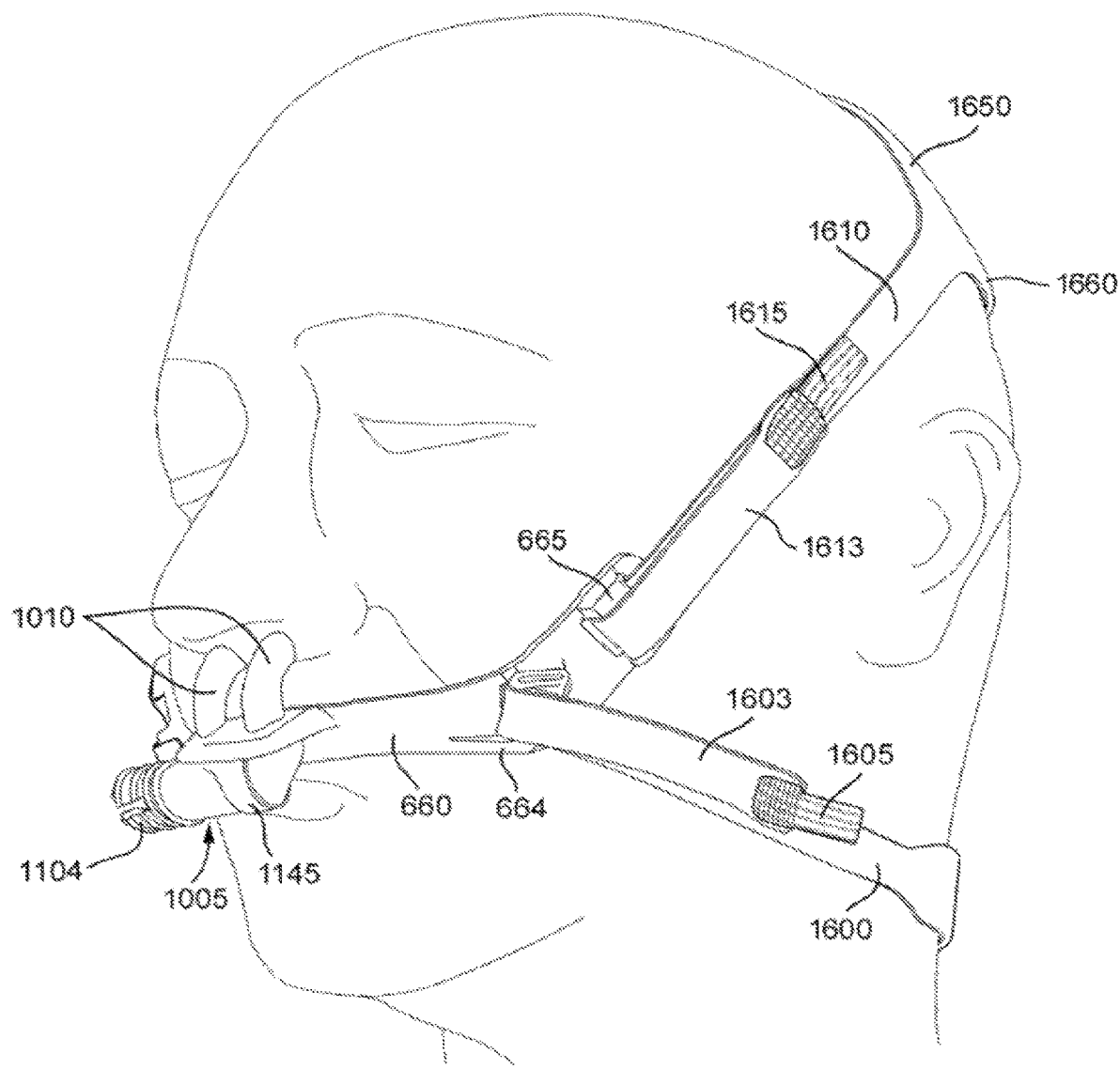
Figure 22I:
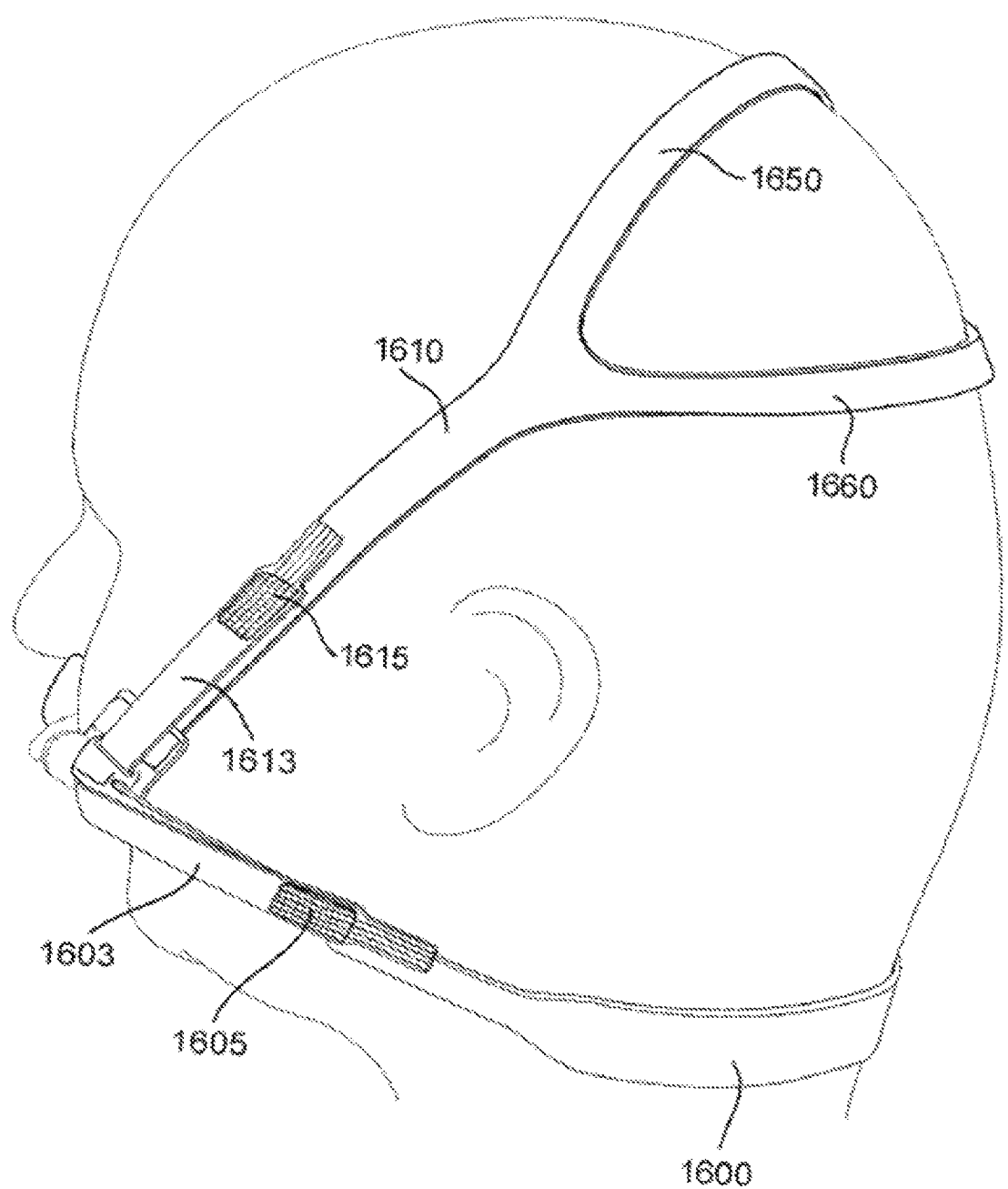
Figure 22J:
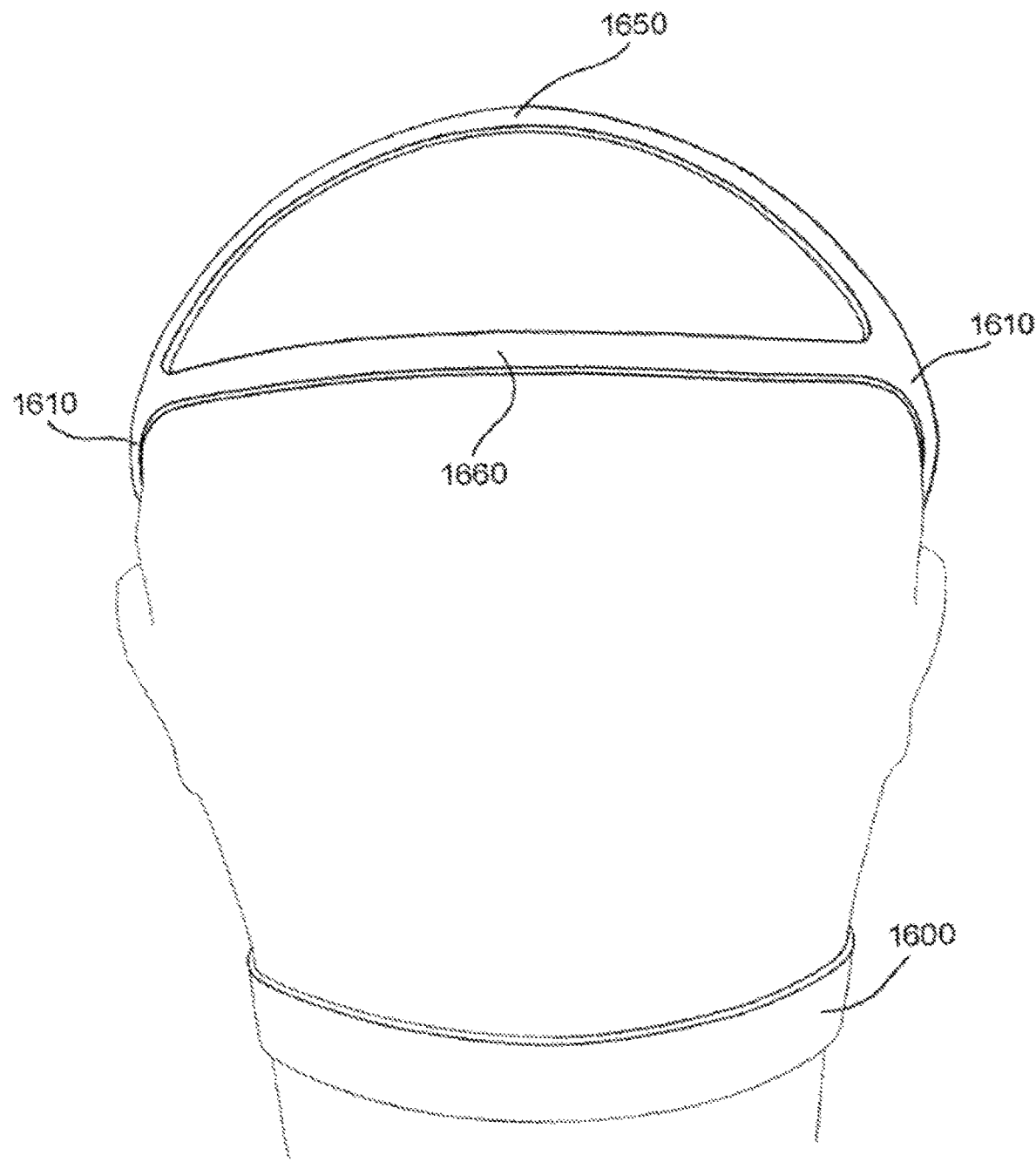

The following description is provided in relation to several sample embodiments which may share common characteristics and features. It is to be understood that one or more features of any one embodiment maybe combinable with one or more features of the other embodiments. In addition, any single feature or combination of features in any of the sample embodiments may constitute additional embodiments Referring to FIGS. 22a-22c, an interface system according to another sample embodiment comprises a frame 660 comprising slots 662, 663 and strap guides, or connectors, 664, 665, respectively, configured to connect straps to the frame 660. As shown in FIGS. 22a-22c, the frame 660 includes a mounting boss 1145 configured to mount a barrel 1005 of the patient interface. The barrel 1005 comprises a barrel first portion 1011 provided on the frame 660 and a barrel second portion 1114 configured to be sealingly connected to the barrel first portion 1011 when supported by the mounting boss 1145. A pair of nasal prongs 1010 are provided on the barrel first portion 1011 and are configured to engage the nares of the patient, for example as shown in FIGS. 22d-22h. It should be appreciated that the nasal prongs 1010 may be integrally formed with the barrel first portion 1011, or may be separately attachable to the barrel first portion 1011 as a pair or as individual prongs, as described above.

A tube connector 1104 maybe provided to the barrel 1005 for connection of a tube or cannula that delivers a flow of breathable gas. The tube connector 1104 may be formed integrally with the barrel second portion 1114 as shown in the drawings, or may be separately formed and connectable to the barrel second portion 1114. The tube connector 1104 may comprise a cutout 1105 for a heating wire and a loom channel 1150 for the loom, i.e. the heating ribbon or wire and the sensor cable(s) bundle. The tube connector 1104 may also comprise circumferential ribs 1500 configured to engage the end of the tube or cannula that delivers the flow of breathable gas. The ribs 1500 are shown in the drawings as helical, but it should be appreciated that they may not be helical. The loom channel allows the tube connector 1104 to be compressed such that its diameter is reduced, for example by squeezing the tube connector 1104 between the fingers of the patient or a clinician, thus allowing the tube or cannula to be more easily inserted over the tube connector. Upon insertion of the tube or cannula over the tube connector, the tube connector may be released and resume its uncompressed diameter. The circumferential ribs 1500 will engage the inner diameter of the tube or cannula and form a friction fit.

Referring to FIGS. 16-19, a patient interface according to another sample embodiment of the invention includes a frame 640 configured for connection to straps of a headgear. The frame 640 comprises slots 642 for receiving the end of a strap of the headgear that is looped through the slots 642.

A mounting boss 645 extends from the frame and includes an aperture 64 7 that is configured to receive the second portion 1114 of a barrel 1005 that may be integrally formed with a tube connector 1104. It should appreciated, however, that the tube connector may be provided separately.

A first portion 1011 of the barrel 1005 may be connected to the mounting boss 645 and the pair of nasal prongs 1010 may extend from the first portion 1011 of the barrel. The second portion 1114 of the barrel is inserted through the aperture 647 of the mounting boss 645 and a barrel connector portion 1116 of the barrel first portion 1114 is sealingly connected to the barrel first portion 1011.

Figure 16:
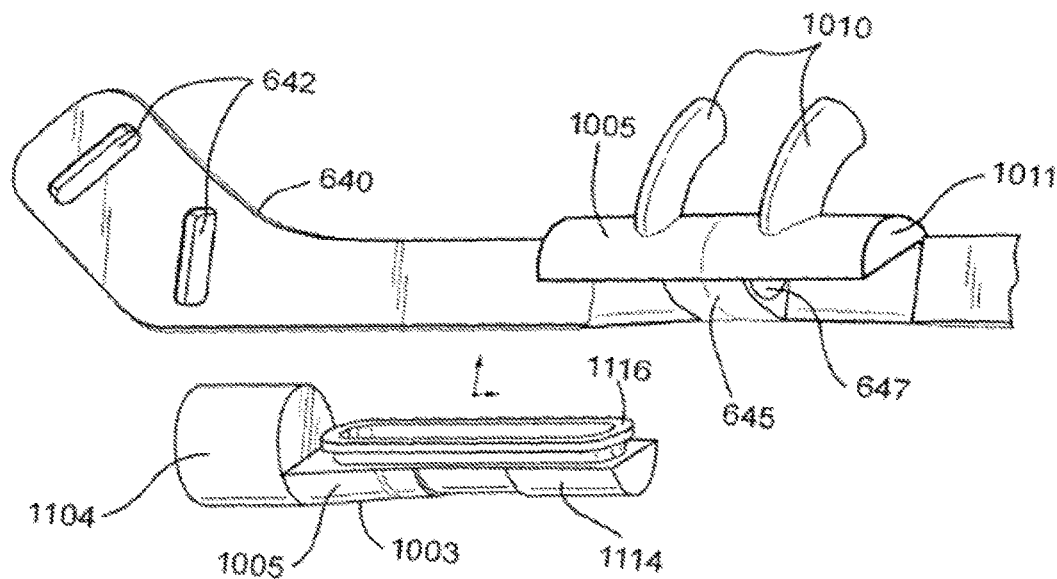
Figure 17:
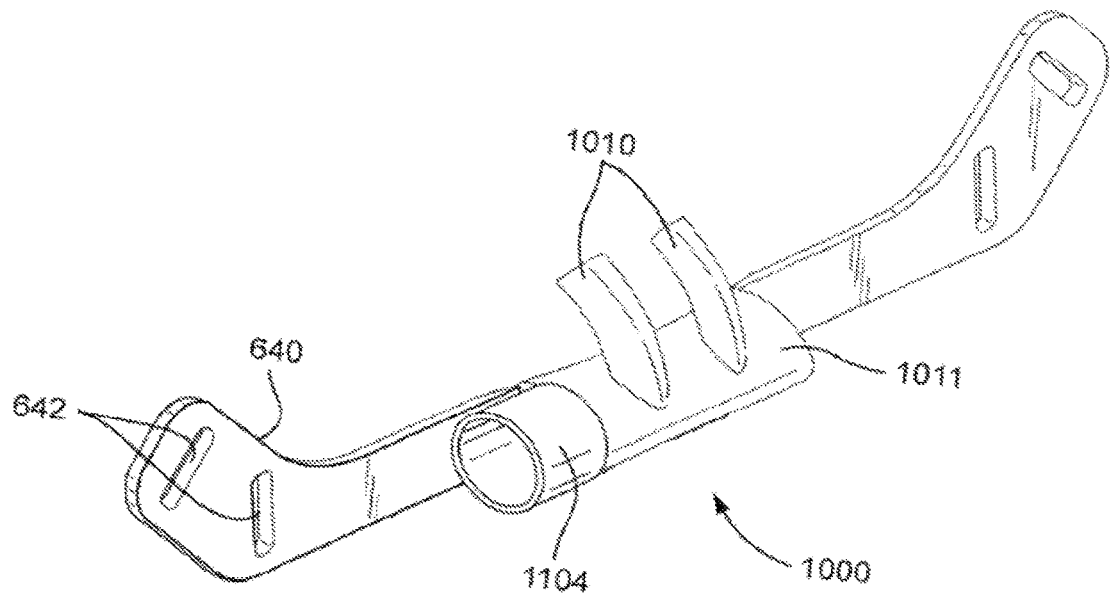
Figure 18:
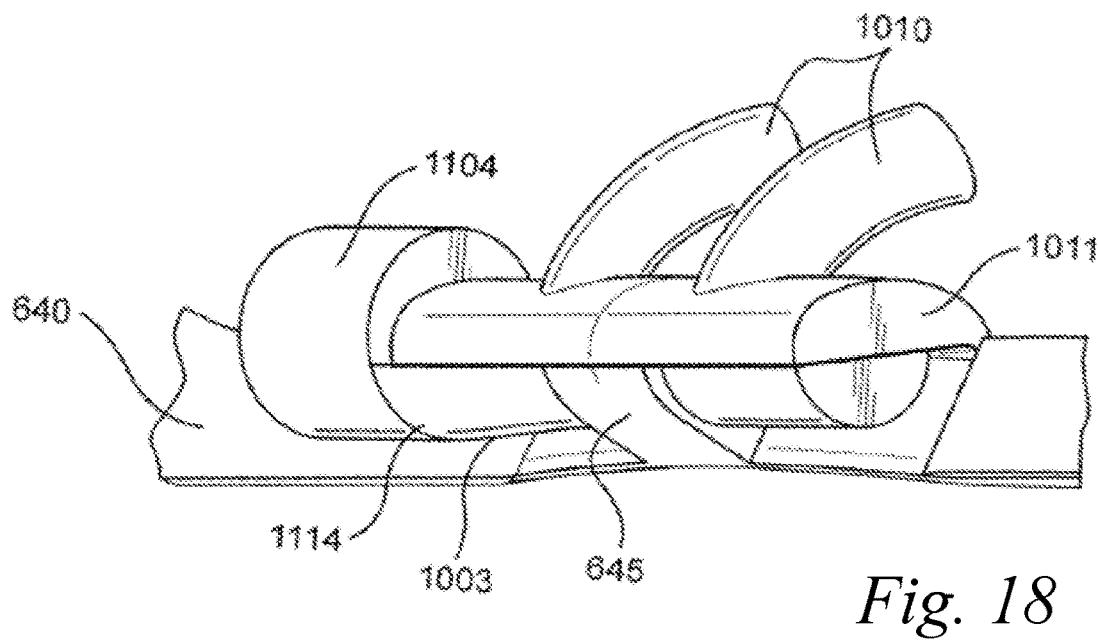
Figure 19:
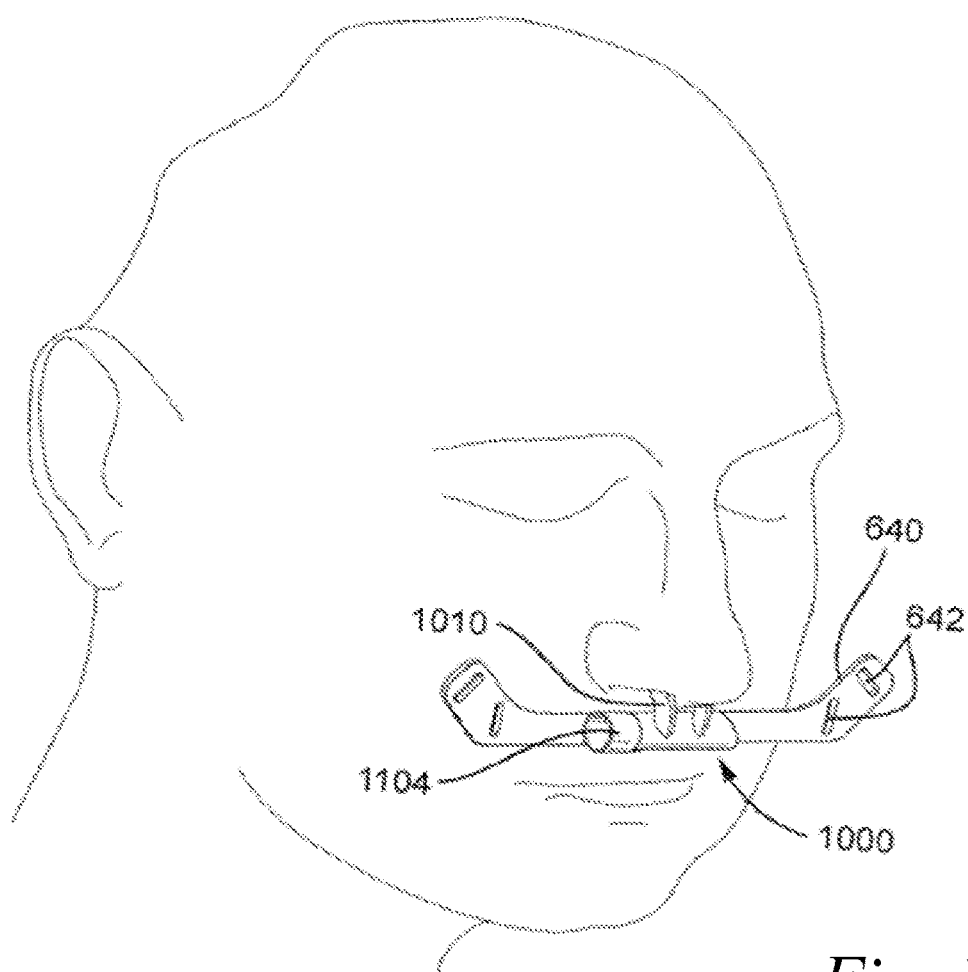

As shown in FIG. 16, the barrel 1005 includes a sloped surface, or ramp, 1003 from a first end of the barrel adjacent the tube connector 1104 to a second end opposite the first end. The ramp 1003 acts to equalize the flow between the nasal prongs 1010.

Referring to FIGS. 20 and 21, the patient interface may comprise a frame 1200 that pivotally receives the barrel 1005. The frame 1200 may comprise flexible extending members 1210 that each comprise connectors 1215 formed on an end thereof. The flexible members 1210 are each flexible generally about a plane 1217. A headgear 650 may comprise apertures 655 that each hook on to a respective connector 1215 of the flexible members 1210. In an alternative form, connectors 1215 may be provided to the headgear 650 and apertures 65 5 may be provided to the flexible members 1210 so that a reverse hook connection is possible. As shown in FIG. 21, the connection of the frame 1200 to the headgear 650 holds the frame 1200 in a stationary position while the barrel 1005 of the patient interface is pivotable with respect to the frame 1200 to permit adjustment of the nasal prongs 1010. The tension of the straps of the headgear 650 is not transmitted through the frame 1200 to the barrel 1005 of the patient interface.

The headgear 650 may be formed of fabric and plastic, for example, a laminate of fabric and plastic. The tube connector 1104 may also be formed, for example, of plastic as well as the frame 1200. The barrel 1005 and the nasal prongs 1010 may be formed, for example, of silicone.

The interface may be donned, or removed, by the patient by pulling the connected headgear and patient interface over, or off, the patient's head. The interface may also be donned, or removed, by connecting, or disconnecting, a connector 1215 with, or from, an aperture 655 of the headgear 650.

Figure 8:
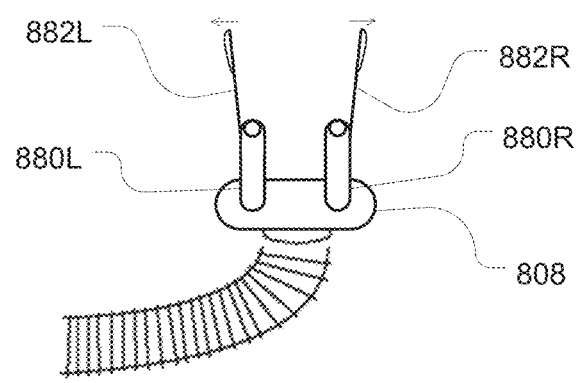
FIG. 8 is an illustration of an embodiment of a patient interface with internal nasal dilators for insertion within a patient's nares.

In some embodiments, the patient interface or cannula may be implemented with a nasal dilator, such as an internal or external nasal dilator. Illustrations of example embodiments are shown in FIGS. 8 to 11. In the embodiment of FIG. 8, dilator extension members 882R, 882L project from a patient interface such as a portion of a cannula 808 body. For example, the extension members may project from prongs 880R, 880L of the cannula 808 as illustrated in FIG. 8. In such a case, the prongs serve as dilator mount portion of the cannula or patient interface. The extension members in FIG. 8 are sized to project inside nares of a patient's nose even if the prongs 880L, 880R also do not extend within the nares. Such extension members may then be formed or shaped to ply an expansion force against an internal surface of each nare. This expansion force, which is illustrated by the arrows in FIG. 8, permits the extension members to assist with keeping the nasal passages dilated from inside the nares. Thus, the extension members may be formed of a material that is flexible and resilient to provide a dilation force. However, these extensions may otherwise be configured with one or more spring elements (not shown) to provide a suitable expansion force with more rigid extension members.

Figure 9:
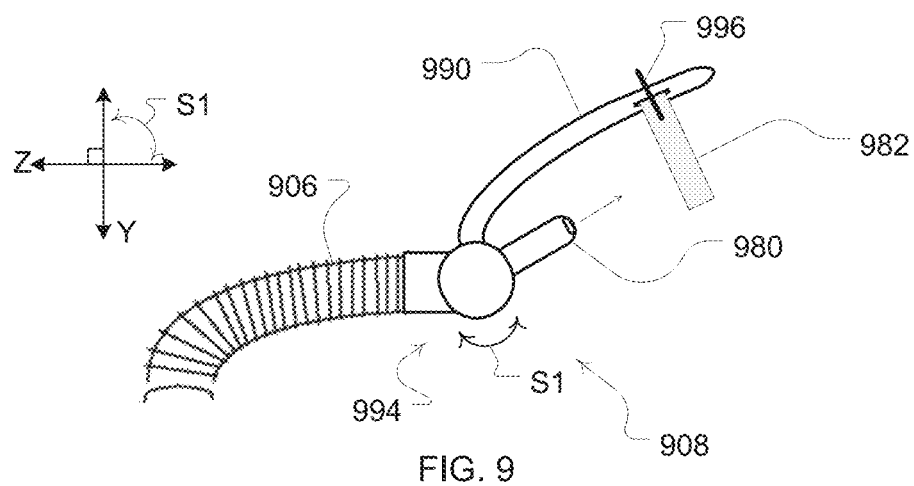
FIG. 9 is a side view illustration of another example embodiment of a patient interface with external nasal dilators for contact with an external surface of the patient's nose.
Figure 10:
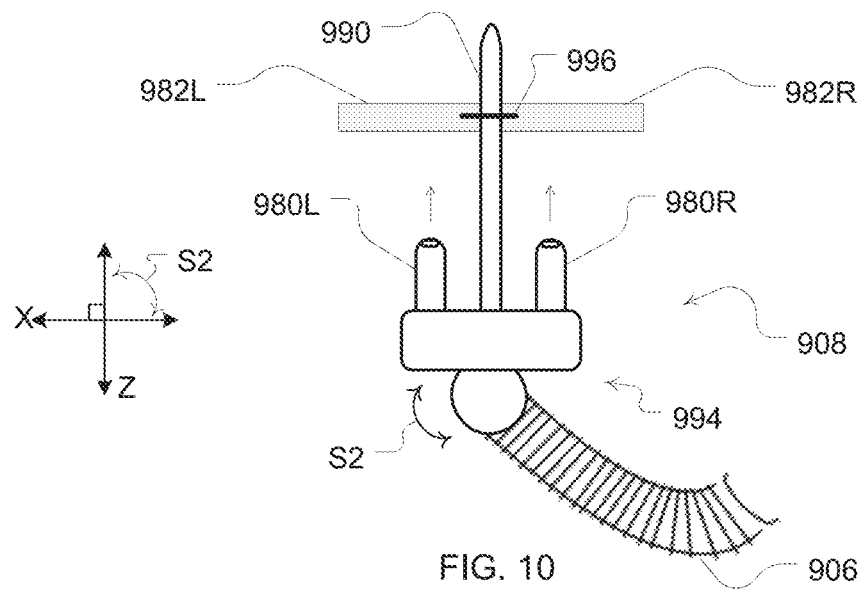
FIG. 10 is a top view illustration of the example patient interface of FIG. 9.
Figure 11:
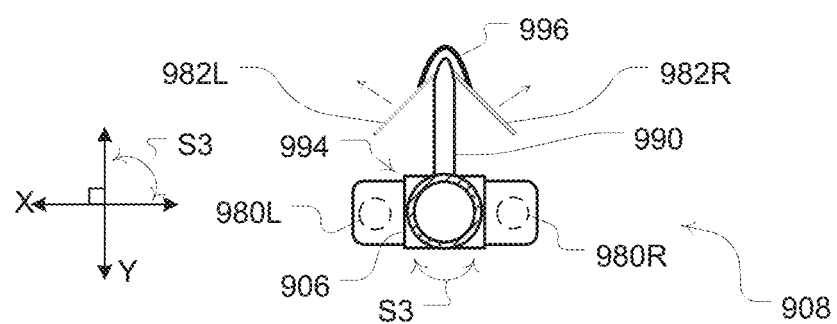
FIG. 11 is a front cross-sectional view illustration of the example patient interface of FIG. 9.

In some embodiments, the extension members of the patient interface may be formed to ply an expansion force from an exterior surface of a patient's nares. An example of such an embodiment is illustrated in FIGS. 9-11. In such an embodiment, the extension members 982 may comprise a dilator strip or strips. For example, a portion of the patient interface or cannula 908 may include a bridge support 990. The bridge support may be flexible for adjustment so that it may conform to the nose shapes of different patients. When the cannula is in place to provide gas flow to the nares of a patient, the bridge support may extend from the cannula so that the bridge support is proximate to a ridge area of a patient's nose. The support may then serve as a dilator mount portion to permit the dilator extension members to be mounted thereto and positioned proximate to the exterior surface of the patient's nose.

For example, the bridge support 990 may optionally include a gap or clip so that a disposable dilator strip may be releasably retained by the bridge support 990. In such an embodiment, a disposable dilator strip may be inserted or coupled to the bridge support for use. Such a dilator strip may then be a flexible and resilient material so as to permit placement at opposing external surfaces of the nose of the patient and yet still be able to ply the expansion force at those surfaces to assist with dilation of the nares by pulling at the exterior surfaces of the nose. Thus, these strips may also typically include an adhesive so that a surface of the dilator strip may adhere to opposing exterior surfaces of the nose. Thus, a left side dilator strip 982L and a right side dilator strip 982R may then be adhered to the left and right sides of the patient's nose respectively. With such embodiments, the extension members may serve the purpose of securing the cannula or patient interface in a suitable position for providing a flow to the nares of the patient with prongs 980, 980R, 9080L as well as providing a dilation force to assist with keeping the patients nasal passages open during a use of the patient interface. Moreover, although not shown in FIGS. 8-11, additional components of the patient interface may be provided for further securing of the cannula in the desired position for use, such as the cannula arms previously discussed.

In some embodiments, the extension members 982L, 982R may be more permanently constructed with the bridge support by, for example, forming the dilator strip as an incorporated portion of the patient interface or bridge support of the cannula 908. Thus, rather than replacing disposable exterior dilator strips as previously discussed, for each use a suitable adhesive may be re-applied to the nasal surface sides of the attached or incorporated dilator strip.

In some embodiments, an optional spring element 996 may also be provided with the dilator strip. For example, where extension members themselves are not formed to have a sufficient resilience to provide the expansion force, the spring element, when coupled with the extension members, may serve to provide the expansion force with the extension members 992R, 992L. In the example of FIG. 9, a wire or other resilient component may serve as the spring element.

As further illustrated in FIG. 9, the patient interface may also include one or more swivels. A swivel 994 can permit the patient interface or cannula 908 to remain in a desirable position for directing the flow to the nares of the patient if a patient moves during sleep. Thus, a swivel provides relative movement between an air delivery portion of the patient interface and a delivery tube portion of the patient interface. For example, one or more swivels may permit relative rotation between a cannula 908 and delivery tube 906 about one or more different axes (illustrated as perpendicular axes X, Y, Z). As illustrated in the embodiment of FIG. 9, a swivel may permit a rotation of the cannula 908 with respect to the delivery tube 906 along arrows S1 or about an imaginary X axis. Such movement can permit an air delivery portion of the cannula (e.g., prongs 980) to vertically rotate with respect to the delivery tube 906.

Similarly, as illustrated in the embodiment of FIG. 10, a swivel 994 may permit a rotation of the cannula 908 with respect to the delivery tube 906 along arrows S2 or about an imaginary Y axis. Such movement can permit an air delivery portion of the cannula (e.g., prongs 980L, 980R) to horizontally rotate with respect to the delivery tube 906.

Finally, as illustrated in the embodiment of FIG. 11, a swivel may permit a rotation of the cannula 908 with respect to the delivery tube 906 along arrows S3 or about an imaginary Z axis. Such movement can permit an air delivery portion of the cannula (e.g., prongs 980L, 980R) to tilt rotation with respect to the delivery tube 906.

5.2 Humidifier, Heater and Tube

Breathable gas is supplied to the patient by a blower (104 of FIG. 1), which may be integrated with other elements of the apparatus, or from a reticulated source, or from bottled gas, or otherwise. The air may be filtered at the input to the blower (104) or at some other point in the gas flow path. Optionally, the apparatus may also include a humidifier and/or heater (112, 111) and a delivery tube heater (135) (or apparatus to regulate heat loss from the delivery tube 106). In the case of a heated delivery tube, insulation material may be provided on the tube to prevent the heat from the tube from bothering the patient or otherwise being transferred to the skin of the patient. Such a tube may be wrapped with an insulating material or the tube material may be selected for is insulation properties. For example, the delivery tube may be increased in thickness to provide or increase its insulating effect. The heater device 111 may be exposed to a water mass and/or to the breathable gas flow. For example, the humidifier device may include a reservoir or fluid circuit for passing the breathable gas through or proximate with a fluid or vapor of the reservoir or fluid circuit. One or more heating elements (not shown separately from heater 111) may be provided to warm the fluid to create the vapor and/or to warm the breathable gas by convection. The warming device may further include a pump for circulating fluid within the reservoir or a fluid circuit of the patient interface or blower. For purposes of regulating the temperature and/or humidity of the warming element, the apparatus may also include humidity sensors (117, 121, 134), and/or temperature sensors, and/or a flow rate sensor, and/or pressure sensors. The sensor(s) generate temperature and/or humidity signals and/or a flow rate signal, and/or pressure signals (illustrated in FIG. 1) for controlling the humidifier and/or heater and/or tube heater using control logic (120) to maintain the temperature and/or humidity of the breathable gas delivered to the patient. In some applications, this device can be controlled to alter the temperature and humidity of the breathable gas such that the delivery conditions are within the acceptable or preferred ranges as stated above.

Generally, it has been found that some available devices are slow when changing the level or degree of humidification due to the need to heat a relatively large mass or water. However, in embodiments of the present technology, two air streams may be provided, namely a first relatively dry air stream in one flow channel, and a second relatively moist air stream in another flow channel. By mixing the streams to a third flow channel, the level of humidification of the air delivered to the patient may be rapidly changed as necessitated by the settings of the apparatus.

Figure 2B:
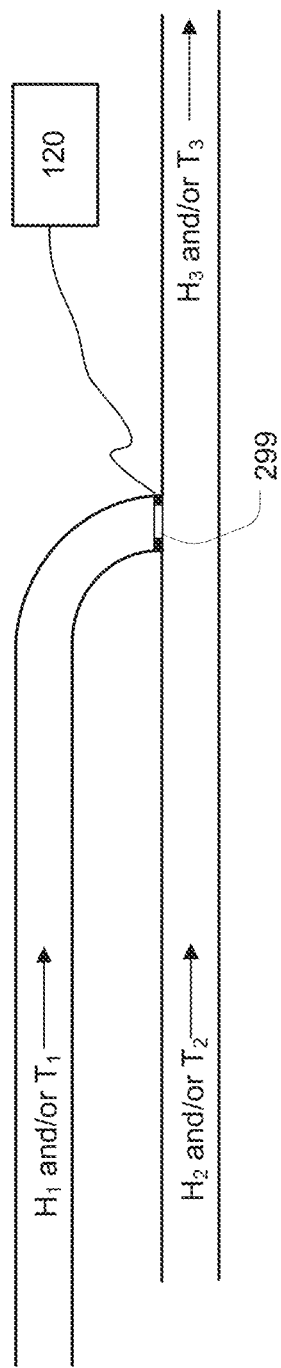
FIGS. 2A and 2B illustrate embodiments of a gate valve for adjusting temperature and/or humidity of the treatment provided by an apparatus of the present technology.
Figure 2A:
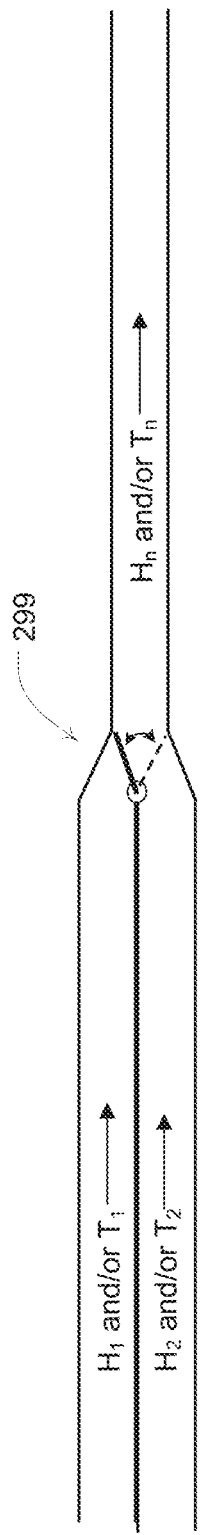

One means of achieving this is to employ an active flow gate 299 as illustrated in the examples of FIGS. 2A and 2B. For example, if FIG. 2A, when the flow gate is in one position, it directs flow from the blower to a path that provides for one desired level of temperature and humidification of the breathable gas, and in an alternate position directs flow from the blower to another path that provides a significantly different level of temperature and humidification of the breathable gas, optionally with no humidification. The flow gate may be controlled to switch flow direction in response to breathing cycle phase, or otherwise under control of the controller 120. Optionally, the flow gate may be controlled to activate to a position that allows the splitting or mixing of the flow between the two paths. For example, based on the desired humidity and/or temperature settings measured by one set of sensors in a combined tube, the controller may adjust the flow gate to mix variable amounts of gas of two distinct flow paths at two different humidity and/or temperature settings, which may be separately controlled by readings from two additional and different sets of sensors. Another version of the flow gate that allows for mixing of flows is illustrated in FIG. 2B with a controllable iris valve. Other mechanisms of generating and mixing flows of different temperatures and humidities, such as dual blower supply, may be used.

By way of further example, by controlling the flow gate in conjunction with detected changes in the patient's respiratory cycle, a lower humidity and/or temperature gas may be delivered during patient expiration and a higher humidity and/or temperature gas may be delivered during patient inhalation. Alternatively, a higher humidity and/or temperature gas may be delivered during exhalation. Thus, such flow control of the humidity of the breathable gas delivered to the patient can generate high temperature and/or humidity delivery only when the patient requires such for therapeutic reasons, for example during an inhalation phase of a breathing cycle. This controlled delivery in turn may allow for a reduction in the power and/or water requirements of the apparatus over the duration of a therapy session. Detection of the phases of the respiratory cycle of the patient may be based on an analysis of data from an appropriate sensor such as the sensors discussed in more detail herein.

Figure 4:
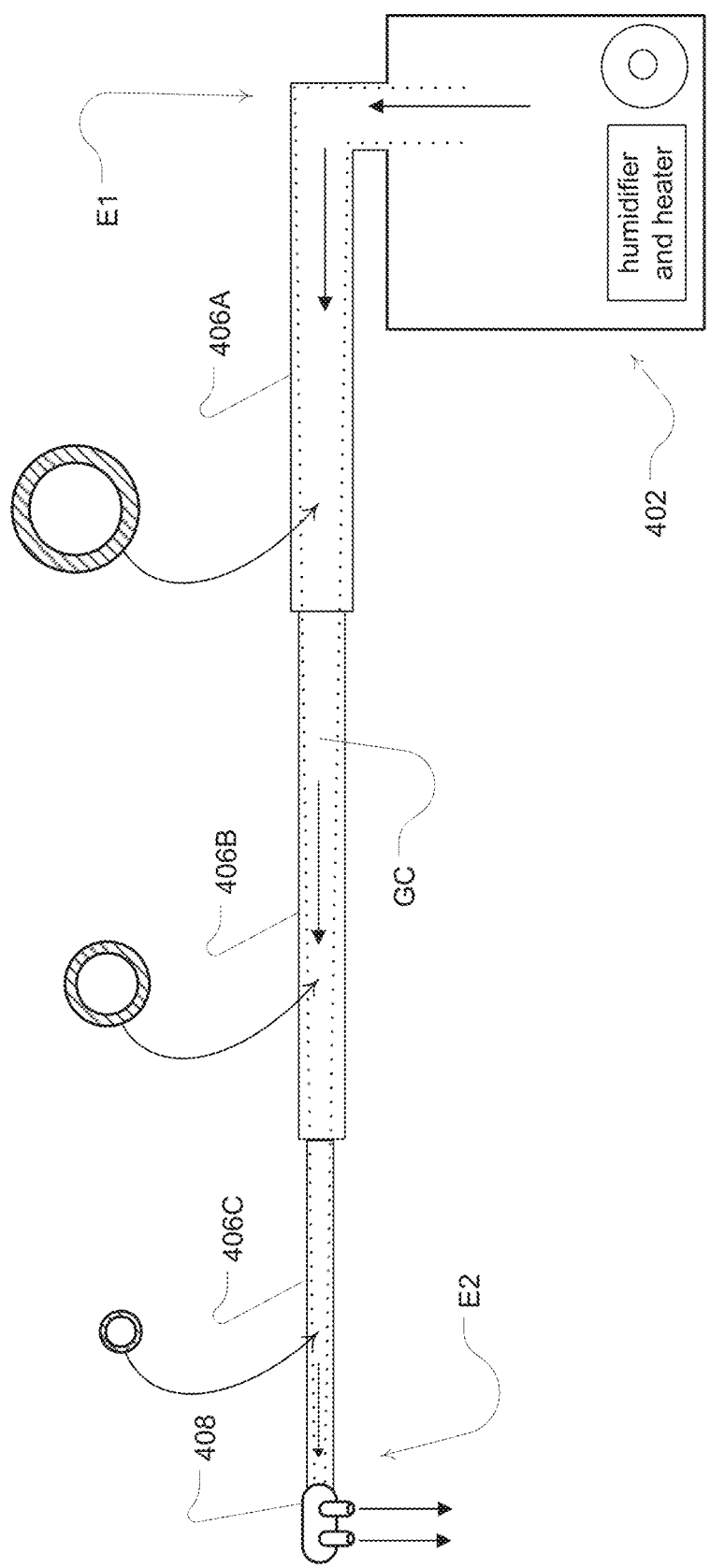
FIG. 4 shows an example decreasing airflow channel diameter of a delivery conduit for a flow source of the present technology.

In one embodiment, shown in FIG. 4, the delivery conduit 406A, 406B, 406C from the airway treatment device may be formed with a gas delivery channel that has a decreasing cross section or diameter. A reduction in the cross section diameter can reduce the impedance of the delivery tube and may also reduce heat loss. For example, as illustrated in the embodiment of the delivery conduit of the open airway treatment device 402 of FIG. 4, an internal airflow channel GC of the delivery conduit decreases from at least one larger cross sectional area portion shown as delivery conduit 406A to at least one smaller cross sectional area portion shown as conduit 406B to a yet smaller cross sectional area portion shown as delivery conduit 406C proximate to the nasal cannula 408. In this way, for a given flow resistance, the tube diameter proximal to the patient can be smaller than with a constant diameter tube. Further, the tube section 406A, and optionally 406B, may be heated (not shown) to control the breathable gas temperature and/or humidity to a level that allows for the change in temperature of the breathable gas through 406C such that the delivered gas to the patient is within the desired range. The small tube section of 406C reduces the heat transfer between the breathable gas and the environment compared with the larger sections of 406B or 406C.

The cross sectional area of any portion of the airflow channel would typically be smaller than the cross sectional area of the airflow channel of the upstream portion of the delivery conduit. To avoid undesired flow restriction and/or noise, transitions between these different cross sectional portions of the delivery conduit may be made by gradual blending at or near their intersections. Additional tube portions may be interposed between 406A and 406B to provide for more gentle transitions in diameter.

In one embodiment, the end portion of the delivery conduit near the flow generator may have an internal airflow channel cross section diameter of about 8-15 mm. Such an embodiment may also end with an airflow channel having a cross sectional area diameter of about 3-6 mm proximate to the nasal cannula. Such a delivery conduit may optionally be formed as a foam silicone tube to provide improved thermal insulation properties.

5.3 Sensors

In some embodiments, the airway treatment delivery device may optionally include one or more flow sensors 116. For example, flow through the nasal cannula 108 may be measured using a pneumotachograph and differential pressure transducer or similar device such as one employing a bundle of tubes or ducts to derive a flow signal. Although the flow sensor is illustrated in FIG. 1 in a location proximate to the blower, the flow sensor may optionally be located closer to the patient, such as in the patient interface or nasal cannula 108.

The airway treatment device may also optionally include one or more pressure sensors 114, 131, such as a pressure transducer. The pressure sensor(s) 114, 131 can be configured to measure the pressure generated by the blower 104 and/or supplied at the nasal cannula or patient airway. In the illustrated embodiment, the pressure sensors 114, 131 are proximate to the blower and located downstream of the blower proximate to the patient interface. For example, one or more pressure sensors may be located in the prongs or body of the nasal cannula. The pressure sensor(s) 114, 131 generates a pressure signal(s) indicative of the measurement(s) of pressure at its particular location. Such a signal(s) can be utilized in settings or calculations of the device. The pressure sensor 114 has only been shown symbolically in FIG. 1 since it is understood that other configurations and other components may be implemented to measure the pressure associated with the blower 104. For example, the pressure may be deduced from knowledge of the blower performance characteristics and the operating blower current and/or voltage and/or rotational speed and/or flow rate. Optionally, different groups of sensors may be provided for a delivery tube associated with each nare of the nasal cannula. For example, a delivery tube for each nare may include a pressure sensor and/or flow sensor so that independent measurements of flow and/or pressure may be measured for each nare.

The airway treatment device may also include one or more temperature sensors as previously mentioned. For example, such sensors may be located to measure the heater(s) 111, 135, and/or the treatment gas at various locations in the delivery tube such as near the blower (e.g., before or after), after the humidifier and near the patient. Similarly, the treatment device may also include one or more humidity sensors as described above. Thus, humidity may be measured before and/or after the humidifier and near the patient. Additional such sensors may be employed when multiple flow channels are utilized such as in the embodiments of FIGS. 2A and 2B for more measuring of the conditions of the distinct portions of the tubes. Still further sensors may also be configured to measure ambient humidity and temperature.

5.4 Controller

The signals from the various sensors (when present) may be sent to a controller or processor 120. Optional analog-to-digital (A/D) converters/samplers (not shown separately) may be utilized in the event that supplied signals from the sensors are not in digital form and the controller is a digital controller. Based on input signals from these sensors and/or other optional sensors, the controller may in turn generate blower control signals. For example, the controller may generate an RPM request signal to control the speed of the blower 104 by setting a desired frequency or rotational velocity set point and comparing it with the measured condition of a frequency or velocity sensor. Alternatively, such changes may be based on determining a desired flow set point and comparing it with the measured condition of the flow sensor. Typically, such changes to the motor speed are accomplished by increasing or decreasing supplied motor current with the servo based on determined differences between set and measured conditions such as in a closed loop feedback fashion and translating the difference to current. Thus, the processor 120 or controller may make controlled changes to the flow delivered to the patient interface by the blower 104. Optionally, such changes to flow may be implemented by controlling an exhaust with a mechanical release valve (not shown) to increase or decrease the exhaust while maintaining a relatively constant blower speed.

The controller or processor 120 is typically configured and adapted to implement particular control methodology such as the methods described in more detail herein. Thus, the controller may include integrated chips, a memory and/or other control instruction, data or information storage medium. For example, programmed instructions encompassing such a control methodology may be coded on integrated chips in the circuits or memory of the device or such instructions may be loaded as software or firmware using an appropriate medium. With such a controller or processor, the apparatus can be used for many different open airway treatment therapies, such as the flow treatments previously mentioned, by adjusting a flow delivery equation that is used to set the speed of the blower or the exhaust venting by an optional release valve (not shown). Thus, flow may be set to desired levels as set by the switches of the device and optionally increased in response to detected respiratory conditions such as an apnea, hypopnea, or airway resistance. The flow rate may be kept substantially constant over the phases of respiration. In some embodiments, the generated flow may be kept generally constant over the respiratory cycle and provide some end expiratory relief. Alternately, in some embodiments the flow may be varied smoothly to replicate the patient's detected respiration cycle.

In another example embodiment of the device, indications of upper airway obstruction determined by the controller are servo-controlled by varying the flow rate and/or level of humidification and/or temperature. For example, a device in accordance with the technology monitors the patient for signs of partial or complete upper airway obstruction. Upon detection of partial upper airway obstruction, and according to the severity and frequency of such events, the level of humidification is increased. In some embodiments, if the partial airway obstruction is eliminated, or not detected, the level of humidification may be reduced. Similarly, if partial airway obstruction is detected, flow may be further increased.

In one embodiment of the technology, indications of the need to vary treatment are derived from a pressure signal that is in turn used to infer patient flow in the controller 120. The inferred flow estimate is applied to automatic pressure control algorithms such as those described in U.S. Pat. No. 5,704,345, the entire contents of which are hereby expressly incorporated by cross-reference. The output of the automatic pressure algorithms is however, in one embodiment, used to control the flow rate and/or level of humidification and/or temperature.

In other forms, pressure is used directly by the controller to determine the presence of partial or complete airway obstruction. In other forms, other non-pressure, non-flow based diagnostic techniques are used, such as movement of the suprasternal notch, patient movement, sympathetic nervous system activation (e.g. sweating, skin resistance, heart rate), pulse oximetry, EEG and ECG. Such additional diagnostic devices may be configured with the apparatus to provide measurement data to the controller.

In one embodiment, the controller may determine a tidal volume or inspired volume of air or gas by the patient during treatment. Such a determination may be used for setting the pressure or flow and/or analyzing conditions of the patient's airway or respiration. In view of the venting or unsealed nature of the patient interface that permits the external flow, the tidal volume ($V_P$) may be determined by measuring the volume of air delivered by the blower ($V_O$) and measuring or determining the volume of leak air ($V_L$) associated with the nasal cannula and subtracting the latter from the former (e.g., $V_O - V_L = V_P$). In some embodiments, the patient interface may seal with the patient nares but have a pre-determined venting characteristic, or one that may change as a function of the pressure or flow rate setting of the flow generator. Thus, the volume of leak may be determined by a look-up table or calculation by the controller 120 based on the settings of the flow generator.

5.5 Other Aspects of the Apparatus

In other embodiments of the technology, the apparatus can be combined with additional components like accessories, which may be attached to pre-defined interfaces or using the shape of the embodiment, openings, screw holes, or other coupling methods or prominent areas of the apparatus to attach. These accessories can be for example additional filters, or sound dampening mechanisms, or data logging electronics, which may have for example either a mechanical, pneumatic, magnetic and/or electrical connection to the apparatus. The connection and interaction may also be wired so that the accessories work together with the apparatus from a distance.

Figure 3:
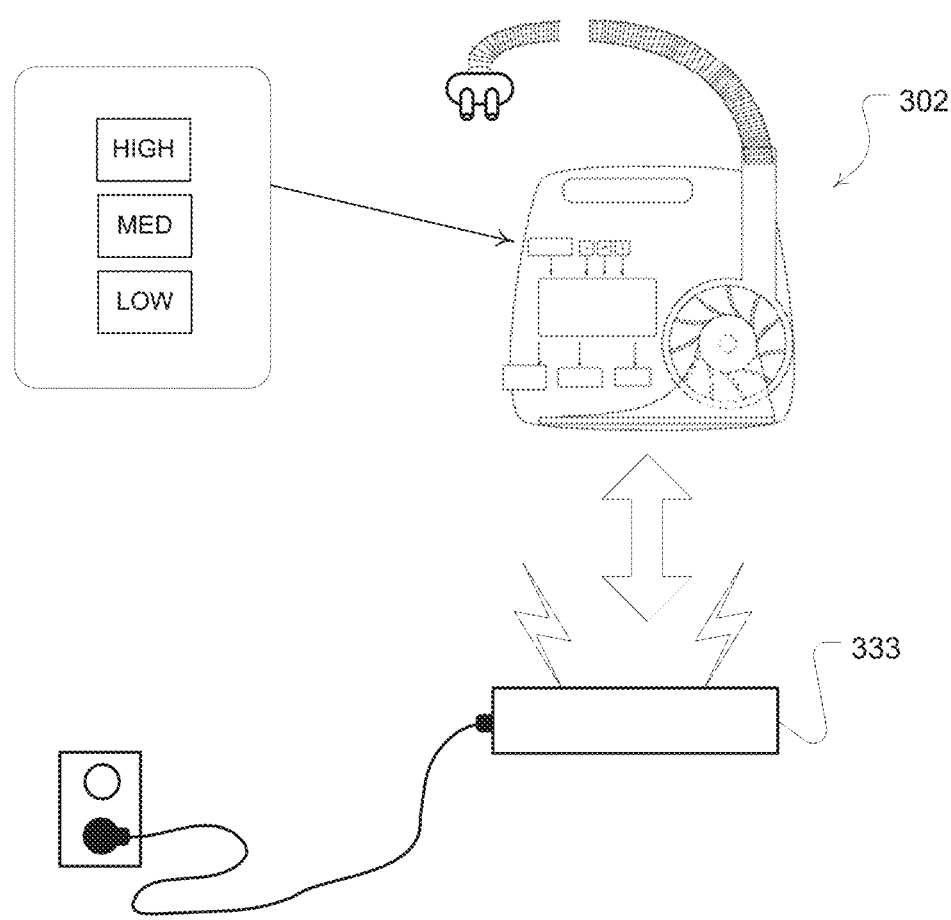
FIG. 3 shows a rechargeable embodiment of an apparatus for treatment according to an embodiment of the present technology.

One example is a chargeable battery pack as illustrated in FIG. 3. The airway treatment device of this embodiment may be implemented with a DC battery sufficient to permit at least a use for a single sleep session without connection to an AC power outlet. A dock 333, such as a cradle with a docking port charger that may be releasably coupled with a charging port of the respiratory treatment device 302, provides a convenient way to charge the battery of the respiratory treatment device 302.

Other accessories can add additional features to the devices or modify the existing feature set, for example by using a new method for motor control to reduce noise. For example, a noise sensor or microphone may be provided to detect levels of noise generated by the blower or the patient interface. Noise measurements may be made and an increase in ambient noise (e.g., a level of sound after filtering out frequencies such as the frequencies that may be associated with snoring) may be responded to by the controller 120 changing a motor speed in attempt to reduce the noise. However, the controller may further reject such changes to the extent that any change would prevent a minimum desired level of treatment from being generated by the flow generator for the patient.

5.6 Warm-Up Methodology

One practical consideration in the design and operation of the apparatus described herein is that the humidification apparatus may comprise an arrangement whereby a mass of water is required to be increased or decreased in temperature. This, in turn, may result in some delay between the change in the heater state and the humidity and/or temperature of the breathable gas delivered. When such a delay prevents the desired combination of flow, temperature and humidity to be met in the delivered gas, it may be desirable to prioritize the properties that are to be met for therapeutic, comfort or functional reasons. For example, it may be desirable to ensure that humidity is within the preferred range as the first priority, temperature is within the preferred range as the second priority, and flow is within the preferred range as the third priority.

Figure 5:
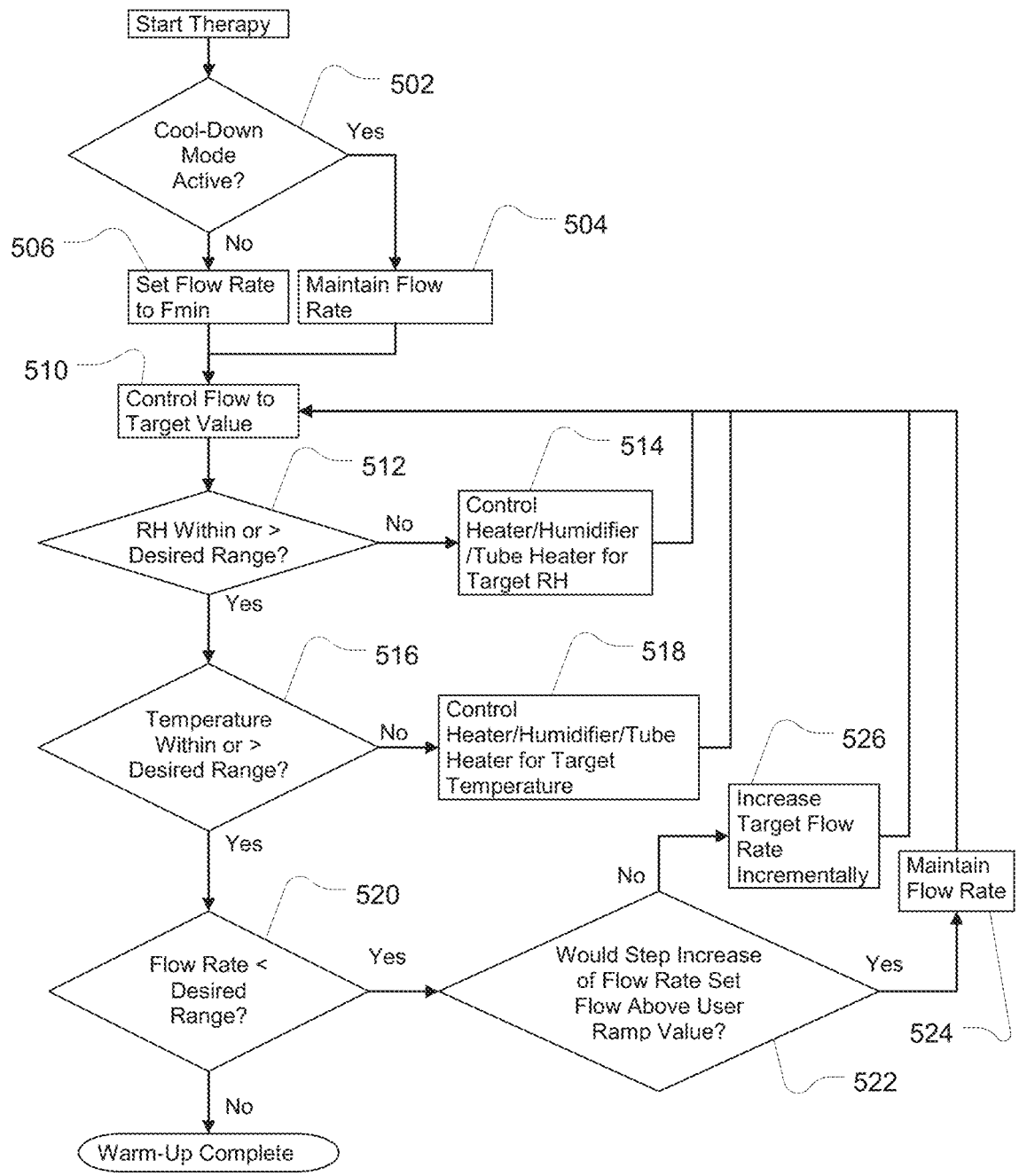
FIG. 5 is an example flowchart describing the control of the apparatus in warm-up mode.

Such prioritizing can be accomplished by the logic sequence described in FIG. 5. The flow rate Fmin is a small flow of about 5%-35% of the desired therapy flow—sufficiently large to transport the breathable gas to allow sensing and control, but sufficiently small to ensure that the patient does not suffer any discomfort as a consequence of the delivered sub-optimal breathable gas.

Optionally, this sequence may be initiated conditionally upon, and/or triggered by, detection of a patient connected to the apparatus. Such detection may be by observation or detection of fluctuations in pressure and/or flow signal(s) and other techniques such as those described in U.S. Pat. No. 6,240,921 (ResMed Limited), the contents of which are hereby expressly incorporated herein by cross-reference.

In addition to control of the flow to meet the desired delivered breathable gas property ranges, it may also be desirable for the patient to control the flow of the apparatus in a manner that allows the flow rate to increase in accordance with a selected rate. Such control may offer advantages in acceptance and compliance of such therapy because the patient is able to become accustomed to the therapy over a longer time than would be the case without such rate control.

This start-up strategy may be applied for a cold-start or a warm-start. As shown in FIG. 5, an example algorithm monitors the temperature and humidity delivered at the patient interface (either directly or calculated from other inputs), for example by means of temperature and humidity sensors 132 and 134, and ramps up the temperature as quickly as possible to the desired range (while maintaining relative humidity (RH) within the desired range). Then the flow rate is increased from the initial value to the desired value in accordance with the user ramp setting such that the delivered temperature and humidity are maintained within the desired ranges.

The algorithm of FIG. 5 may be further described as follows. At 502 of FIG. 5, the start-up procedure determines if the apparatus is in a cool-down mode. If the result is affirmative, the flow rate is maintained in 504. Otherwise, a minimum flow rate will be set in 506. Process moves to 510 where the flow of the apparatus is controlled to meet the target or set point. The method then proceeds to 512 where the relative humidity (RH) is measured and compared to a desired range or deviation of the target or set point for relative humidity. If the result in 512 is negative then the process proceeds to 514 to control the humidity related elements of the apparatus to the set point or target for relative humidity. The process then advances to 510 to control the breathable gas flow rate. If the result is affirmative in 512 then process advances to 516. In 516, the breathable gas temperature is checked to see if it is within a desired range or deviation from the target or set point value. If the result in 516 is negative then the process proceeds to 518 to control the temperature related elements of the apparatus to the set point or target for temperature. The process then advances to 510 to control the breathable gas flow rate.

If the result in 516 is affirmative, then the process proceeds to 520. In 520, the flow rate is checked to see if it is below a desired range or acceptable deviation from the therapy target flow rate. If, in 520, the result is negative then the process is complete. If, in 520, the result is affirmative then the process advances to 522. In 522, the flow rate is measured or calculated to determine if a step increase in the rate is appropriate for ramping up of the flow rate. If the step increase would raise the flow rate above the therapy target, then process flows to 524 and 510 without an increase in the target set point of the flow rate for the warm-up process. If in 522 a step increase would not raise the flow rate above the therapy target, the target set point is incremented to increase or ramp up the flow rate in 526 and then controlled in 510 at the new stepped-up flow rate. In this way, the ramping of flow rate may be governed without allowing the humidity or temperature to deviate from their desired or target set-points.

Figure 6:
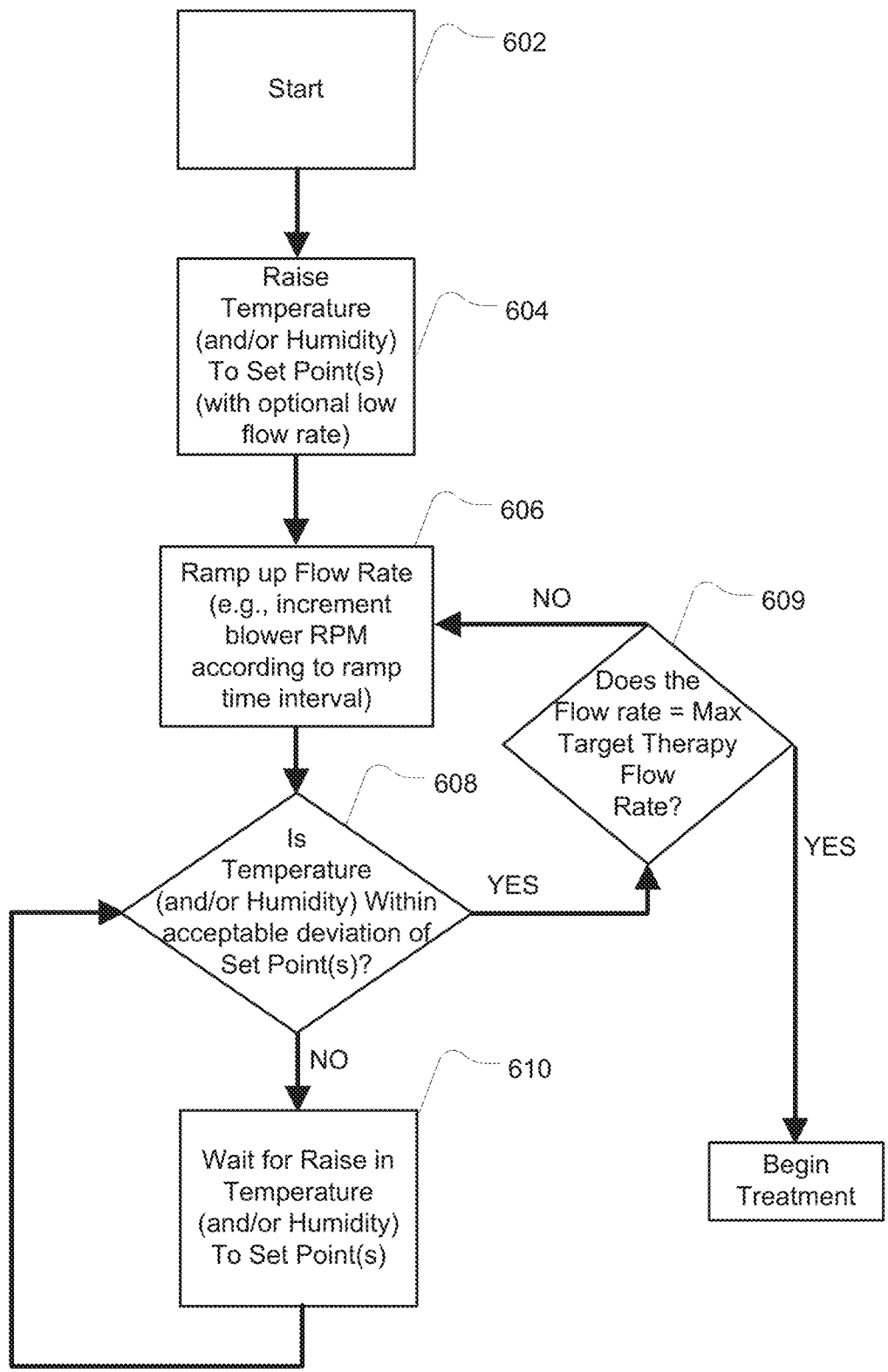
FIG. 6 is another example flowchart describing the control of the apparatus in warm-up mode.

Another example start-up procedure algorithm is illustrated in FIG. 6. At 602 the start up procedure begins. In 604, the temperature (and/or humidity) of one or more heating elements (e.g., humidifier heating element) is set and allowed to raise to the desired set point as determined by a temperature and/or relative humidity sensor. Once the set temperature and/or humidity setting has been reached, at 606, a ramp-up procedure for the flow generator begins in which an incremental increase in the flow rate will be set over toward a maximum, such as by setting an incremental increase in the RPM set point of the blower every several minutes. At 608, the temperature and/or humidity levels are checked with the appropriate sensors to determine if the temperature and humidity is within an acceptable deviation margin of the set point after an increase in the blower flow rate. If the margins are acceptable (e.g., a margin of +/−1, 2, 3, 4 or 5 degrees of the temperature setting or +/−1, 2, 3, 4 or 5% relative humidity of the humidity setting) the process will flow to 609 to check if the ramp-up of flow has reached the target therapy level for the treatment session. If not, then the process returns to 606 to again increment the flow generator according to the ramp-up procedure and its time adjustment period. If, in 609, the therapy level has been reached, the warm-up process is complete and the therapy session protocol may begin.

However, in 608, if the levels are not within a predetermined margin of the set points, the measurement/comparison process flows to 610 to wait a period of time. Process then returns to the comparison process of 608 to again check the temperature and/or humidity sensors for compliance with the deviation margin. In this way, the flow rate of the apparatus may ramp up in a comfortable fashion to the therapy flow rate setting while maintaining the desired set points for the humidity and/or temperature of the gas delivered by the apparatus.

5.6.1 Re-Ramp Methodology

In some situations, during the course of therapy with the apparatus a patient may desire a temporary decrease in the flow rate to permit the patient to more comfortably fall asleep with a lower flow rate before the flow rate would then return to a higher prescription or therapeutic level during sleep. Thus, in some embodiments of the apparatus, a re-ramp methodology may be implemented by the controller. The apparatus may permit the user to activate the re-ramp procedure by a switch, button, knob or other user interface of the apparatus. Thus, upon activation of the procedure, the apparatus would lower the flow rate for a predetermined period of time. The period of time may optionally be adjustable by the user with an input device of the apparatus. At the conclusion of the period of time the flow rate may then return to the therapeutic level. Alternatively, it may gradually return to the therapeutic level over the period of time or after a period of time. However, in the event that humidification is also provided during the particular therapy session, additional elements of the control of the re-ramp procedure may be implemented as a function of the presence of humidification and/or heating so as to assist with avoiding rainout or condensation.

For example, in a typical embodiment, the re-ramp algorithm or methodology of the apparatus may only permit the re-ramp feature to be activated after the apparatus has achieved a warmed-up state, such as if the apparatus has already completed the warm-up procedure previously described. Similarly, in an embodiment, the re-ramp feature may be disabled if the apparatus has achieved a cool down state such as at a time after completing a cool-down methodology or when the apparatus is performing a cool-down methodology as described in more detail herein. Thus, the methodology of the re-ramp feature may be implemented as a function of humidification and/or temperature or a humidification state and/or temperature state of the apparatus. In the event that a cool-down state has been achieved, such as with the following described cool-down methodology, and/or the re-ramp feature is disabled, the apparatus may then be re-activated by execution of the warm-up methodology previously described rather than the re-ramp procedure.

In some embodiments, the selection of the rate for the reduced flow during the re-ramp procedure may be user adjusted or selected with an input device or user interface of the apparatus. Additionally, in some embodiments the reduced flow rate may be a function of humidity and/or temperature such that the reduced flow rate selection is at least partially set in a manner that prevents condensation from forming in the patient interface and/or delivery tube. For example, the algorithm may monitor the temperature and humidity internal and/or external to the apparatus, for example by means of temperature and humidity sensors, and then automatically select a reduced flow rate, such as from a look-up table based on the temperature and/or humidity information.

In some embodiments, the reduced flow may be implemented without a blower speed change by the flow generator. In such an embodiment, an exhaust vent or release valve, which may be a mechanical valve that is controlled by a processor or controller of the apparatus, may be opened to vent part of a humidified gas supply from the blower so that only a portion of the humidified flow generated by the flow generator is directed to the patient interface. In this way, a lower humidified flow rate may be delivered to the patient for the re-ramp procedure. The vent or release valve may then close, such as gradually over a period of time that is typically longer than several breaths, to return the humidified flow to the therapeutic rate. Although not shown in FIG. 1, such a release valve or exhaust vent may, for example, be positioned to exhaust gas flow generated by the blower 104 at a position in the air deliver circuit after the humidifier 112.

5.7 Cool-Down Methodology

Another consequence of the practical consideration described above is that the immediate power-down of the apparatus may lead to condensation in the apparatus—particularly the tube—because the heated water mass will continue to emit vapor and so the regions where the breathable gas path is in thermal contact with the environment, for example the tube walls, may cool rapidly. The presence of condensation in the apparatus will adversely affect the comfort and/or function of the apparatus at a subsequent start-up, because droplets may be blown down the tube to the patient interface causing patient discomfort, and/or the presence of water in the heated tube may lead to additional humidification in the breathable gas delivered to the patient or otherwise affect the ability of the system to control the breathable gas delivery at the patient interface within the desired ranges.

An aspect of the current technology is a control methodology that may be optionally used with the apparatus to control the rate of cooling of the apparatus—especially the tube—to diminish the likelihood of significant condensation forming during apparatus power-down.

Such a strategy includes implementing a sequence of apparatus states or transitions to promote the maintenance of the temperature of the breathable gas in the system above the local dew-point temperature. Optionally, this sequence may be initiated conditionally upon, and/or triggered by, detection of the absence of a patient connected to the apparatus. Such detection may be by detection of fluctuations in pressure and/or flow signal(s). The initiation of this sequence may be delayed by a predetermined period, which may be patient-selectable, following such triggering, to allow for temporary disconnection and reconnection of the apparatus. The predetermined period may be about 1-30 minutes.

Figure 7:
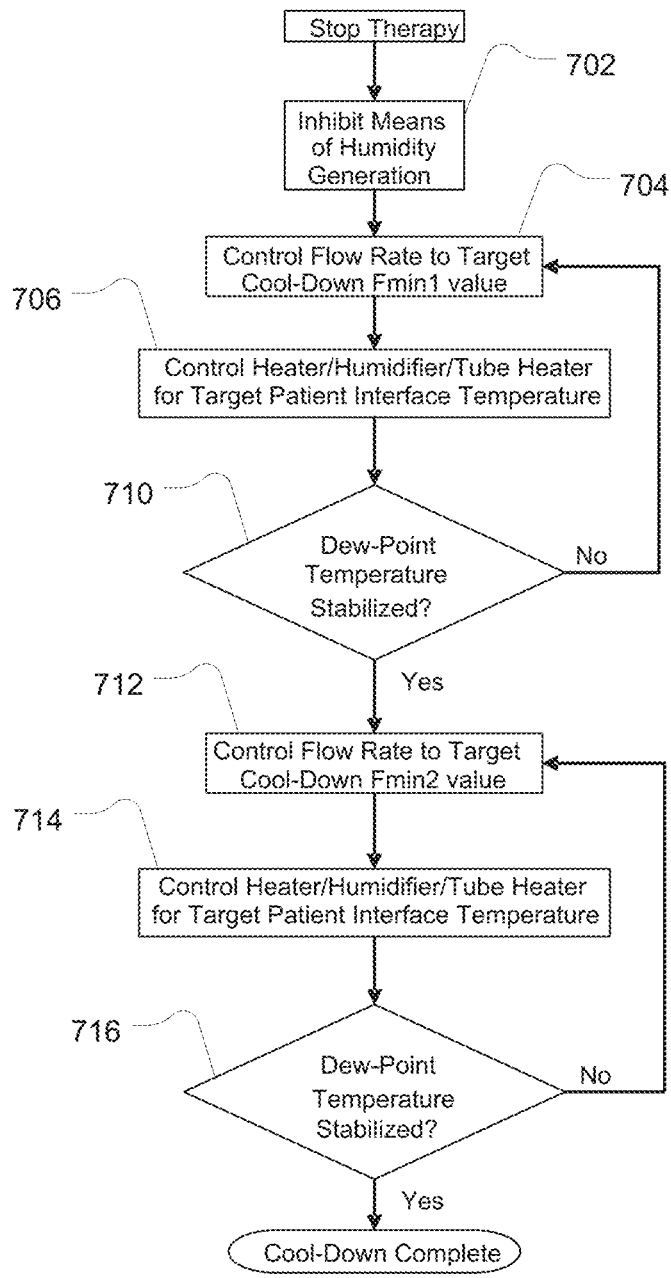
FIG. 7 shows a flowchart describing the control of the apparatus in cool-down mode.

This strategy can be accomplished by the example logic described in FIG. 7. The flow rate Fmin1 may be about 50%-150% of the typical therapy flow. The flow rate needs to be sufficiently high to promote cooling of the water mass but not so high so as to generate obtrusive noise. This flow rate may be a fixed value, a value that is directly or indirectly selected by the user, for example should a rapid cool-down be desired, and/or a variable value that follows a profile with time, or with a sensed breathable gas property value such as humidity.

The flow rate Fmin2 is a small flow of about 5%-35% of the typical therapy flow—sufficiently large to transport the breathable gas to allow sensing and control, but sufficiently small that the humidification of the breathable gas is low and does not cause condensation when the apparatus is subsequently powered-down. The transition in flow rate from Fmin1 to Fmin2 may be controlled to a predetermined profile. Fmin2 may be a fixed value, a value that is directly or indirectly selected by the user, for example should a rapid cool-down be desired, and/or a variable value that follows a profile with time, or with a sensed breathable gas property value such as humidity.

This cool-down strategy applies to any mode or phase of operation of the apparatus. Optionally, a pause to therapy may be requested by the user such that the breathable gas conditions are maintained for a short period, for example 1-30 minutes, and if therapy is not restarted within this period, either manually or by the detection method above, then the cool-down strategy will be initiated. As shown in FIG. 7, the algorithm monitors the temperature and humidity delivered at the patient interface (either directly or calculated from other inputs), for example by means of temperature and humidity sensors 132 and 134, and ramps down the humidity as quickly as possible until such time as the system humidity is stable, whilst maintaining an acceptable dew-point margin, for example about a 2-5° C. margin. The margin can be determined from the Saturation Vapour Pressure at the flow temperature, for example using the formulas in ISO Standard 8185 2007. The flow rate is decreased from the initial value to the Fmin2 in a manner that allows the maintenance of the dew-point margin. The apparatus may then be powered-down.

The algorithm of FIG. 7 may be summarized as follows. In 702, after the treatment therapy controlled by the apparatus is stopped, humidity generation with the humidifier is stopped. In 704, the flow rate generated by the flow generator is controlled to the Fmin1 target value. In 706, one or more of the heating elements are controlled to maintain a target temperature in the delivery tube of the patient interface. In 708, a dew-point temperature is checked to assess if it has stabilized. If it has not, process flow returns to 704. If it has, process flows to 710. In 710, the flow rate of the flow generator is then controlled to the target Fmin2 value. In 712, one or more of the heating elements are controlled to maintain a target temperature in the delivery tube of the patient interface. In 714, a dew-point temperature is checked to assess if it has stabilized. If it has not, process flow returns to 710. If it has, process flow of the cool-down procedure is complete.

5.8 Applications of Method and Apparatus

A user will be titrated to determine the optimal flow rate and temperature for treating the user's sleep disordered breathing (SDB). The optimal settings for flow rate and temperature are those that maximize efficacy of the therapy as well as user comfort. For example, the temperature will be set to the highest value within the range capable by the device that is deemed comfortable by the user. The temperature may also be changed to compensate for any droplets of water that may form in the air delivery tube or user interface, for example nasal cannula. The temperature may also be changed to maximize the efficacy of the therapy. For flow, an example would be for the rate of flow to start at the lowest possible by the device. When the user is asleep and SDB events are detected, such as by the controller of the device, the flow rate would be incrementally increased in response to the SDB events (for example, apneas, hypopneas, flow limitation and snoring) to prevent them from repeating and hence maximizing the efficacy of the therapy. Another method would be to set the flow rate to the highest rate that is comfortable for the user when awake. When the user is asleep, the necessary changes in flow rate may be made in response to the SDB events, again to maximize the efficacy of the therapy.

Changes to flow rates and temperature may be done manually, by an observer of the user when they are asleep. For example, by a sleep technologist observing the user using polysomnography (PSG).

Changes to flow rate, gas temperature and/or humidity levels may also occur automatically in response to the SDB events detected by the apparatus. This would be based on an algorithm that incrementally increases the flow rate, gas temperature and/or humidity levels in response to the SDB events. The magnitude of the increase would be governed by the type of the SDB event. For example, the increase in flow rate, gas temperature and/or humidity levels would be greater for an apnea compared to flow limitation which in turn would be greater than the response to snore. Alternatively, incremental decreases in the flow rate, gas temperature and/or humidity levels would occur in response to an absence of detected SDB events after a certain period of time.

The settings of flow rate, humidity and/or temperature may be increased or decreased by the device with some step value by simply detecting whether any one or more of these SDB events occur. Moreover, such adjustments may be a function of the measure of the detected SDB event. For example, a measure of partial obstruction may be a varying index from 0 to 1 where 1 is fully obstructed, 0 is not obstructed and 0.5 if half obstructed. The change in any of the flow rate, humidity and/or temperature may then be a function of the degree of partial obstruction, such as, a function that generates a greater adjustment when there is a larger degree of obstruction and a lesser adjustment when there is a smaller degree of obstruction. In some embodiments, a degree of partial obstruction may be assessed by a flattening analysis of a respiratory flow signal, a roundness analysis of a respiratory flow signal and/or other partial obstruction methodology for assessing of the patient's upper airway.

To assist in the treatment of SDB, in some embodiments the ratio of the outer diameter of the nasal prongs of the patient interface to the surface area of user's nares may be increased or decreased. These changes would be to increase the efficacy and comfort of the therapy.

Once titration has been effected, optionally, the patient may alter the therapy settings manually within a restricted range to improve comfort according to personal choice.

5.9 Cycling

In some embodiments of the technology, the flow and or humidification of air delivered to each nare is individually controlled. For example, a higher flow and/or more humidification may be delivered on one side compared to the other. In one form, each of the air flow & humidification may be individually cycled in a nare. For example, a flow rate may be adjusted in one nare while maintaining a fairly constant flow rate or humidity in the other nare. By way of further example, a high flow rate may alternate between the left nare and a right nare such that when a high rate is directed at one nare, a low rate is directed at the other. In another form changes in flow and/or humidification of air delivered to one nare are synchronized with changes in flow and or humidification of air delivered to the other nare.

The delivery of a higher flow to one nare compared to the other may be to compensate for a user with unilateral nasal obstruction. In one embodiment, the higher flow rate would be delivered to the nare that was not obstructed. This would maximize the efficacy of the therapy. Alternatively, a higher rate may be delivered to the obstructed nare as an attempt to decrease the obstruction. Obstruction may be determined by automatic method of detecting partial obstruction, for example, by analysis of a respiratory flow signal. Such an analysis may be independent for the respiratory flow signal associated with each nare. Alternatively, unilateral partial obstruction may be detected by an increase in a measure of pressure from a pressure sensor associated with one nare with respect to a measure of pressure of another pressure sensor associated with the other nare.

The delivery of more humidification to one nare compared to the other might be to compensate for the higher flow being delivered to one nare because it is less obstructed. Alternatively, more humidification may be delivered to the nare with higher nasal resistance to reduce this resistance. Optionally, while this is occurring, a higher flow may be delivered to the other nare. After the higher nasal resistance is reduced, by more humidification and/or a higher flow rate, and the resistance is equal between the two nares, the humidification and air flow may then be returned to equal delivery to each of the nares. This may be tested by analysis of the relative pressures of the sensors associated with each nare. For example, the flows directed at each nare may be set to be equal and the two pressures associated with the nares may then be checked and compared for substantial equality, which may indicate that there is no unilateral obstruction.

This delivery of different flow can be achieved, for example, by the use of two motors within the device. One motor for each of the two nares with a controller linking both motors. Alternatively, a single motor blower might be used with controlled venting valves in the flow paths for each nare. In such a case, the blower may be set to a desired rate for the highest flow desired for either nare. The flow at the high rate may be delivered to one nare without substantial venting while the blower flow rate to the other nare may be reduced by venting some of the flow of the flow path of the other nare without delivering all of it to that nare. This may be achieved by separately controlling the diameter of an aperture associated with a venting valve of each delivery tube associated with each nare by the controller. Alternatively, one or more variably controlled gate valves may split a single supply tube from a blower into a y-junction. For example, mechanical gate valves, near a y-junction, may then be set to position(s) to gate a portion of the flow to one delivery tube directed at one nare and a portion of flow into another delivery tube directed at the other nare. For example, 60% of the flow may be directed to one nare and 40% of the flow may be directed at the other nare. The gate valve may be controlled to divide the supply rate by other percentages (e.g., 50%/50%, 0%/100% etc.) Essentially, the controller can set the gate valve to divide the flow between the nares by any desired position or aperture setting. An example of suitable gate valves may be comparable to the gate valves illustrated in FIG. 2A or 2B but with the flows traveling in the opposite direction from that illustrated in those figures. Optionally, additional tubes and gate valves may also be added to then adjust the humidity levels directed to each nare tube as previously described with regard to FIGS. 2A and 2B.

Still further, the delivery of different levels of humidification can be achieved, for example, by altering the proportion of air being delivered that comes from the humidifier compared to that from the environment. By increasing the proportion of air from the environment the lower the amount of humidification being delivered to the patient. In such a case, ambient humidification and temperature sensors may be utilized to provide the controller with data concerning these ambient conditions. Alternatively, there may be two humidification systems. One for each nare of the user with a controller linking both humidifiers.

5.10 Dual Rate Operation

In one embodiment of the technology, a dual rate mode of operation may be employed. In this mode, the device is triggered by the inspirational flow of a user, in particular by the flow rate provided at the beginning of inspiration. This flow rate may be detected by inference from the pressure signal, or otherwise, and compared to a predetermined threshold. The threshold may be set to different sensitivities, e.g. high, medium and low. Once a trigger event is detected, a first flow rate is provided. When the inspirational flow of a user, in particular by the flow rate provided at the end of inspiration, falls below another threshold, the device cycles to a second flow rate. The flow rate may be detected as described above. Again, the thresholds for cycling may be set to different sensitivities, e.g. high, medium and low.

In one form of this dual rate operation, the inspiration flow rate is higher than the expiration flow rate. This is a form of expiration flow relief that may improve the comfort of the therapy.

In another form of this dual rate operation, the expiration flow rate is higher than the inspiration flow rate. This may assist in further increasing the end expiratory pressure (EEP) in the upper airway of the user. By increasing the EEP, the efficacy of the therapy may be improved.

As previously mentioned, such triggering may also be utilized to implement first and second distinct humidification levels or first and second distinct breathable gas temperatures according to the detected phases of the patient's respiratory cycle. Thus, the controller may set different gas temperatures and/or different humidification levels depending on the phase of respiration.

5.11 Alternative Therapy

The therapeutic mode described herein, may be implemented in a device also capable of delivering CPAP or APAP therapy. In this case, the mode of therapy delivered by the device may be changed through a button, dial, menu or other control. A change of therapeutic mode might also be associated with changing the air-delivery circuit to that appropriate to the therapeutic mode.

The device may have an indicator, for example an LED, which will illuminate when the device believes it is not satisfactorily treating the SDB of the user based on data logging. For example, the LED would be illuminated when the device recorded SDB events were above a predetermined threshold at the end of a session. This threshold could be set based on the requirements of the treating physician. An example of a threshold would be an apnea and hypopnea index (AHI) greater than 5 per hour of use. The illumination of this indicator based on SDB events would indicate a change to an alternative therapy from that described in this patent to conventional continuous positive airway pressure (CPAP) or automatic positive airway pressure (APAP).

The indicator described above in one case may result in the device of the user being changed to a CPAP/APAP device. In another case, it may indicate that the mode of therapy being delivered by the device be switched, manually, to CPAP/APAP mode. For this the device would be capable of delivering both types of therapy (i.e., that described in this document and CPAP/APAP). In another case, the indicator may lead to an automatic change of therapy mode and the device which is capable of delivering both types of therapy automatically makes the change. The indicator in this instance would be to notify the user that the change had occurred.

5.12 Dislodgement Avoidance and Detection

The relatively high flow rates of the devices and systems may give rise to additional problems relating to patients experiencing problems wherein the nasal cannula are accidently dislodged during operation. These problems may include potential damage to the eyes or face of the patient wherein the high flow rates of air are accidently directed to sensitive parts of the face.

Figure 12:
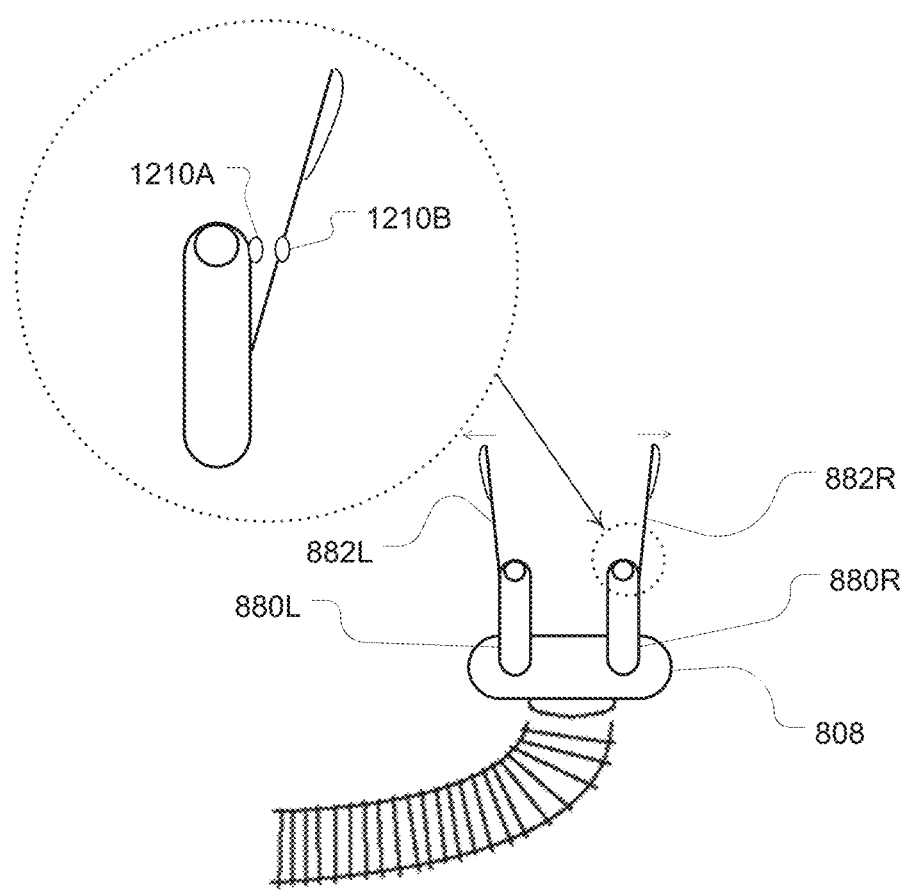
FIG. 12 is an illustration of an example diffuser clip configured with an example disengagement sensor.
Figure 13:
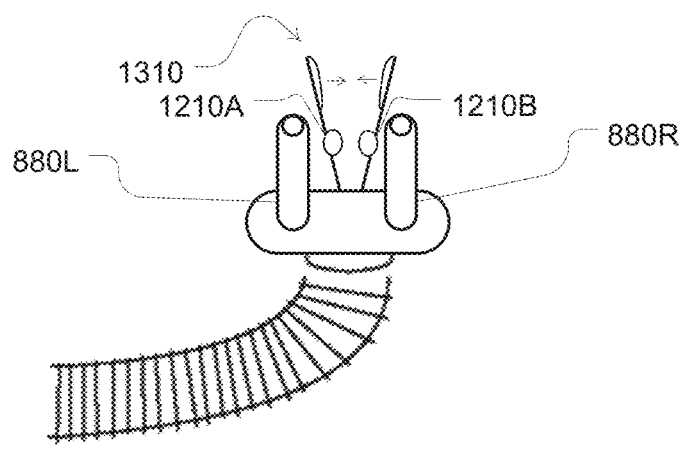
FIG. 13 is a further clip with another example disengagement sensor.

The preferred system and device may also detect accidental dislodgement, wherein the dislodgement is detected by at least one of the aforementioned preferred sensors. When the dislodgement is detected, the system or device may be automatically shut off to prevent or limit potential damage from the high flow rates being accidentally directed to sensitive parts of the patient's face. Alternatively or in addition to the shut off, the dislodgment detection may automatically open a mechanical vent valve controlled by the controller to vent the air at or near the controller or flow generator in a manner that more immediately depressurizes the supply tube to the cannula. One example dislodgement sensor may be a pressure transducer that detects a change in pressure as an indication of dislodgement. In another example, a clip with electrical contacts 1210A, 1210B, such as that illustrated in FIG. 12 or 13, may serve as a dislodgment sensor by sending an electrical switch signal to the controller. During use, the clip may be attached to a portion of the nares, such as at the base of the nose. A light spring force used to hold the clip in place may also be utilized to activate the sensor upon dislodgment. Upon removal or dislodgment, the clip may be configured to spring closed (or open depending on its desired configuration). The closing of the contacts (or opening thereof depending on the configuration of the switch and the spring action) may then be detected electrically by the controller as a dislodgment. The clip may even be combined with the other components of the patient interface such as the nasal dilators previously discussed (e.g., the dilator of FIG. 8 or 11), and may even also serve to maintain the cannula in place as described further herein.

In this regard, the chance or likelihood of accidental dislodgement may also be minimized by attaching a specialized clip 1310 onto the nasal cannula. The clip may be constructed of flexible and resilient material (including polyermic materials) and may attach and secure the nares of the patient to the nasal cannula with a retaining force, and may still maintain a non-sealed relationship between the nose and nasal cannula.

Figure 14:
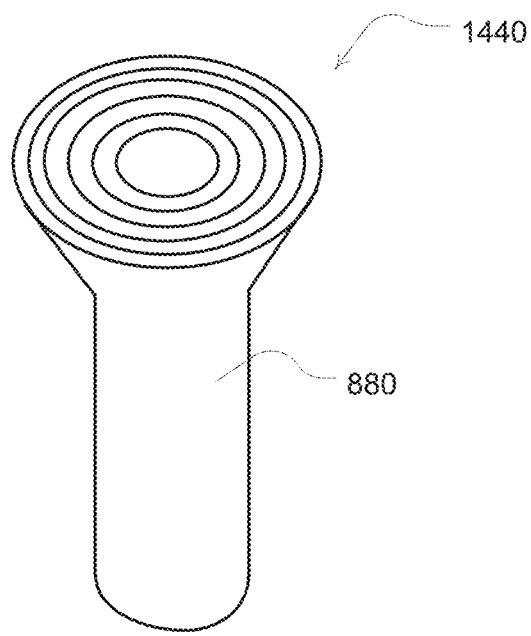
FIG. 14 illustrates an example diffuser for a prong of a nasal cannula.

Also in some embodiments, the end of the nasal cannula that may be inserted into the nose during operation may include an air diffuser such as the example diffuser with radial fins 1440 on the prong 880 illustrated in FIG. 14. Preferably, the air diffuser may prevent or limit the flow of air in a single direction but increases the dispersion of air exiting the nasal cannula. This may serve as an additional safety feature, wherein the nasal cannula are accidentally dislodged from their position in nares. If the dislodgement occurs, the air diffuser reduces the risk that relatively high flow air will directed into a sensitive region of the patient's face such as the eyes. Even if the air is accidentally directed into the eyes of the patient, the attachment of the air diffuser may significantly reduce the overall flow of air directed into the eyes and thereby increase safety of the device and reduce the overall risks.

In situations where the nasal cannala is dislodged while in operation, and this is detected by sensors attached to the system, the system or device may include a controller that sounds and/or displays an alarm to alert a patient or clinician to the dislodgement.

5.13 Cannula Design Modification

The nasal cannula previously described for use with any of the aforementioned embodiments may further include noise limiting features. These noise limiting features may reduce the overall noise heard by the patient and people around the patient, wherein the system or device is operational.

In some embodiments, these noise limiting features may include specialized baffles mounted on or in the nasal cannula or prongs to disperse or diffuse any noise emitted by the nasal cannala. This may be particularly true when the nasal cannula are delivering relatively high flow rates when compared to standard closed CPAP devices.

Figure 15:
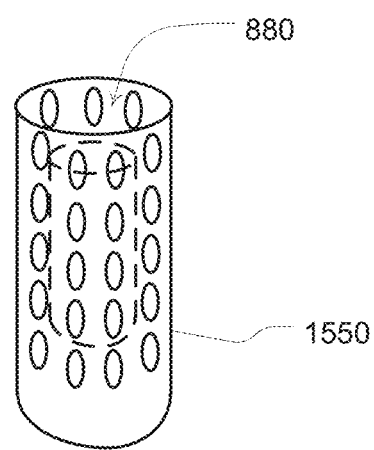
FIG. 15 is an illustration of a baffle for a prong of a nasal cannula.

The noise baffle may be constructed of a foam insert, a maze-like structure mounted on or proximal to the end of nasal cannula engaging the nares of the patient. An example, baffle 1550 about a prong 880 is illustrated in FIG. 15.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, a device in accordance with the present technology could provide nasal CPAP. In one form of the technology, drug delivery is provided with the supply of breathable gas, for example in the form of a nebulised drug. For example, the present system may be used for treatment of COPD or Cystic Fibrosis and accompanied with appropriate drugs for the respective diseases.

The invention claimed is:

1. A system for providing high flow respiratory therapy to a patient, the system comprising:
  a nasal interface configured to deliver a flow of pressurized breathable gas to the patient, the nasal interface comprising:
    a pair of nasal inserts to be inserted into the nares of the patient without sealing against the nares; and
    an inlet through which the pressurized breathable gas is received;
  a conduit to provide the flow of pressurized breathable gas to the nasal interface, the conduit comprising:
    a distal end portion configured to be connected to a supply of pressurized breathable gas;
    a proximal end portion configured to be connected to the inlet of the nasal interface;
    a tube heating element to heat gas within the conduit; and
    a set of conduit sensors located at the proximal end portion of the conduit, the set of conduit sensors comprising (i) a first temperature sensor to generate a first temperature signal indicating a temperature of the gas within the conduit and (ii) a first humidity sensor to generate a first humidity signal indicating a level of humidification in the gas within the conduit; and
  a respiratory treatment device to generate the flow of pressurized breathable gas to provide high flow respiratory therapy to the patient, the respiratory treatment device comprising:
    a housing;
    a blower positioned within the housing to draw air from an ambient environment around the housing and to generate a pressurized flow of gas, the blower including an impeller that generates the pressurized flow of gas;
    a set of device sensors located proximate to the blower within the housing, the set of device sensors comprising (i) a second temperature sensor to generate a second temperature signal indicating a temperature of the pressurized flow of gas and (ii) a flow sensor to generate a flow signal indicating a flow rate for the pressurized flow of gas;
    a humidifier to humidify the pressurized flow of gas, the humidifier comprising (i) an inlet to receive the pressurized flow of gas, (ii) a water reservoir to hold a volume of water and through which the pressurized flow of gas passes to add humidification, (iii) a heater to warm the water contained in the water reservoir, and (iv) an outlet through which the pressurized flow of gas with humidification is output as the pressurized breathable gas to be delivered to the patient via the conduit and the nasal interface;
    an air inlet in the housing through which the blower draws the air from the ambient environment;
    a gas supply that is coupled to the air inlet upstream of the blower, the gas supply supplying supplemental gas to the blower so that the supplemental gas is mixed in the blower by the impeller with the air from the ambient environment, wherein the pressurized flow of gas generated by the blower comprises the supplemental gas mixed with the ambient air by the impeller; and a controller to control operation of, at least, the blower, the heater, and the tube heating element to provide high flow therapy to the patient, the controller being configured to control the operation of the blower, the heater, and the tube heating element based on, at least, the first temperature signal, the first humidity signal, the second temperature signal, and the flow signal.

2. The system of claim 1, wherein the supplemental gas comprises oxygen.

3. The system of claim 1, wherein the controller controls operation of, at least, the blower, the heater, and the tube heating element so that a humidification range for the pressurized breathable gas provided to the patient includes up to 100% humidification.

4. The system of claim 1, wherein the controller controls operation of, at least, the blower, the heater, and the tube heating element so that a range of flow rates for the pressurized breathable gas provided to the patient includes up to 50 liters/minute.

5. The system of claim 1, wherein the controller controls operation of, at least, the blower, the heater, and the tube heating element so that a range of flow rates for the pressurized breathable gas provided to the patient includes a top flow rate that exceeds 50 liters/minute.

6. The system of claim 1, wherein:
the controller controls operation of, at least, the blower, the heater, and the tube heating element so that a humidification range for the pressurized breathable gas provided to the patient includes up to 100% humidification, and
the controller controls operation of, at least, the blower, the heater, and the tube heating element so that a range of flow rates for the pressurized breathable gas provided to the patient includes up to 50 liters/minute.

7. The system of claim 1, wherein:
the controller controls operation of, at least, the blower, the heater, and the tube heating element so that a humidification range for the pressurized breathable gas provided to the patient includes up to 100% humidification, and
the controller controls operation of, at least, the blower, the heater, and the tube heating element so that a range of flow rates for the pressurized breathable gas provided to the patient includes a top flow rate that exceeds 50 liters/minute.

8. The system of claim 1, wherein:
the set of device sensors further comprise a second humidity sensor to generate a second humidity signal indicating a level of humidification for the pressurized flow of gas, and
the controller is further configured to control operation of, at least, the blower, the heater, and the tube heating element additionally based on, at least, the second humidity signal.

9. The system of claim 1, wherein:
the set of device sensors further comprise a pressure sensor to generate a pressure signal indicating a level of pressure for the pressurized flow of gas, and
the controller is further configured to control operation of, at least, the blower, the heater, and the tube heating element additionally based on, at least, the pressure signal.

10. The system of claim 1, wherein:
the set of device sensors further comprise (i) a second humidity sensor to generate a second humidity signal indicating a level of humidification for the pressurized flow of gas and (ii) a pressure sensor to generate a pressure signal indicating a level of pressure for the pressurized flow of gas, and
the controller is further configured to control operation of, at least, the blower, the heater, and the tube heating element additionally based on, at least, the second humidity signal and the pressure signal.

11. The system of claim 1, wherein:
the set of conduit sensors further comprise a pressure sensor to generate a pressure signal indicating a level of pressure for the pressurized breathable gas within the conduit, and
the controller is further configured to control operation of, at least, the blower, the heater, and the tube heating element additionally based on, at least, the pressure signal.

12. The system of claim 1, wherein the respiratory therapy device further comprises:
a third temperature sensor positioned at or around the heater to generate a third temperature signal indicating a temperature of the heater,
wherein the controller is further configured to control operation of, at least, the heater additionally based on, at least, the third temperature signal.

13. The system of claim 1, wherein the conduit is fluidly connected to respiratory therapy device to receive the pressurized breathable gas output from the humidifier.

14. The system of claim 1, further comprising means for connecting the inlet to the conduit.

15. The system of claim 1, further comprising means for connecting the conduit to the respiratory therapy device.

16. The system of claim 1, further comprising means supplying power to the respiratory therapy device and supporting the respiratory therapy device during operation.

17. The system of claim 1, wherein the respiratory treatment device further comprises:
another set of device sensors that are positioned downstream of the humidifier, the other set of device sensors generating post-humidification signals that indicate one or more conditions of the pressurized breathable gas output by the humidifier,
wherein the controller is further configured to control operation of, at least, the blower, the heater, and the tube heating element additionally based on, at least, the post-humidification signals.

18. The system of claim 17, wherein:
the other set of device sensors comprise a third temperature sensor to generate a third temperature signal indicating a temperature of the pressurized breathable gas output by the humidifier, and
the third temperature signal is part of the post-humidification signals that are used by the controller to control operation of, at least, the blower, the heater, and the tube heating element.

19. The system of claim 17, wherein:
the other set of device sensors comprise a second humidity sensor to generate a second humidity signal indicating a level of humidification for the pressurized breathable gas output by the humidifier, and
the second humidity signal is part of the post-humidification signals that are used by the controller to control operation of, at least, the blower, the heater, and the tube heating element.

20. The system of claim 17, wherein:
the other set of device sensors comprise (i) a third temperature sensor to generate a third temperature signal indicating a temperature of the pressurized breathable gas output by the humidifier and (ii) a second humidity sensor to generate a second humidity signal indicating a level of humidification for the pressurized breathable gas output by the humidifier,
the third temperature signal is part of the post-humidification signals that are used by the controller to control operation of, at least, the blower, the heater, and the tube heating element, and
the second humidity signal is part of the post-humidification signals that are used by the controller to control operation of, at least, the blower, the heater, and the tube heating element.

21. The system of claim 1, wherein:
the nasal interface further comprises:
  a nasal interface body with one or more surfaces defining one or more fluid passageways from the inlet to the pair of nasal inserts;
  a left lateral headgear connector extending from a left lateral side of the nasal interface, the left lateral headgear connector including a left front surface that defines a left aperture that extends at least partially through the left lateral headgear connector; and
  a right lateral headgear connector extending from a right lateral side of the nasal interface, the right lateral headgear connector including a right front surface that defines a right aperture that extends at least partially through the right lateral headgear connector; and
the system further comprises:
  a headgear assembly to position the nasal interface below the patient's nares, the headgear assembly comprising a plurality of headgear straps that include at least:
    a left headgear strap with a left end that is configured to connect to the left lateral headgear connector, wherein the left end of the left headgear strap includes a left projection that extends orthogonally from a surface of the left end, wherein the left projection is configured to extend through and engage the left aperture to connect the left headgear strap to the left lateral headgear connector; and
    a right headgear strap with a left end that is configured to connect to the right lateral headgear connector, wherein the right end of the right headgear strap includes a right projection that extends orthogonally from a surface of the right end, wherein the right projection is configured to extend through and engage the right aperture to connect the right headgear strap to the right lateral headgear connector.

22. The system of claim 21, wherein the left projection extends through the left front surface of the left lateral headgear connector when the left headgear strap is connected to the left lateral headgear connector, and
wherein the right projection extends through the right front surface of the right lateral headgear connector when the right headgear strap is connected to the right eft lateral headgear connector.

23. The system of claim 21, wherein the left headgear strap is configured to extend along the patient's left cheek, above the patient's left ear, and to a back of the patient's head,
wherein the right headgear strap is configured to extend along the patient's right cheek, above the patient's right ear, and to the back of the patient's head, and
wherein the left headgear strap and the right headgear strap are connected to each other at a location corresponding to the back of the patient's head.

24. The system of claim 21, wherein the inlet is positioned on a lateral side of the nasal interface body such that, when connected, the conduit extends from the lateral side of the nasal interface.

25. The system of claim 21, wherein engagement of the left aperture and the left projection provides a connection between the left headgear strap and the left lateral headgear connector without loose strap ends around or near the patient's face, and
wherein engagement of the right aperture and the right projection provides a connection between the right headgear strap and the right lateral headgear connector without loose strap ends around or near the patient's face.

26. The system of claim 25, wherein the left lateral headgear connector and the right lateral headgear connector are made of a flexible material.

27. The system of claim 26, wherein the left lateral headgear connector is configured to lay against and conform to a left side of the patient's upper lip and cheek when the nasal interface is in use, and
wherein the right lateral headgear connector is configured to lay against and conform to a right side of the patient's upper lip and cheek when the nasal interface is in use.

28. The system of claim 21, wherein the nasal interface body includes a first barrel portion and a second barrel portion, wherein the first barrel portion is provided on a frame that includes the left lateral headgear connector and the right lateral headgear connector, wherein the second barrel portion includes the inlet and is configured to sealingly connect to the first barrel portion.

29. The system of claim 28, wherein the first barrel portion includes an upper surface and a mounting boss extending downward from the upper surface and connecting to the frame at a position below the upper surface, wherein the mounting boss, the upper surface, and the frame define a loop into which the second barrel portion is configured to be inserted.

* * * * *